(12) United States Patent  
Leonhardt et al.

(10) Patent No.: US 11,052,247 B2
(45) Date of Patent: Jul. 6, 2021

(54) SKIN TREATMENT SYSTEM

(71) Applicant: Cal-X Stars Business Accelerator, Inc., Playa Vista, CA (US)

(72) Inventors: Howard J. Leonhardt, Playa Vista, CA (US); Jorge Genovese, Buenos Aires (AR)

(73) Assignee: LEONHARDT VENTURES LLC, Corona del Mar, CA (US)

( * ) Notice: Subject to any disclaimer, the term of this patent is extended or adjusted under 35 U.S.C. 154(b) by 231 days.

(21) Appl. No.: 16/129,533

(22) Filed: Sep. 12, 2018

(65) Prior Publication Data

US 2019/0015661 A1    Jan. 17, 2019

Related U.S. Application Data

(63) Continuation-in-part of application No. 15/812,760, filed on Nov. 14, 2017, and a continuation-in-part of
(Continued)

(51) Int. Cl.
*A61N 1/32* (2006.01)
*A61H 39/00* (2006.01)
(Continued)

(52) U.S. Cl.
CPC ........... *A61N 1/328* (2013.01); *A61H 39/002* (2013.01); *A61K 8/981* (2013.01); *A61K 8/982* (2013.01);
(Continued)

(58) Field of Classification Search
CPC ...... A61N 1/328; A61N 5/0616; A61N 1/327; A61N 1/326; A61N 1/3629; A61N 1/36002; A61N 1/37205; A61N 2005/0652; A61N 2005/0647; A61N 2005/0648; A61N 2005/067; A61K 8/982; A61K 8/981;
(Continued)

(56) References Cited

U.S. PATENT DOCUMENTS 4,622,952 A   11/1986 Gordon
4,976,733 A   12/1990 Girardot
(Continued)

FOREIGN PATENT DOCUMENTS

CA   2685161 A1   10/2007
EP   0603451 A1    6/1994
(Continued)

OTHER PUBLICATIONS

Anne Trafton, "A Noninvasive Method for Deep Brain Stimulation," MIT News Office, (available at http://news.mit.edu/2017/noninvasive-method-deep-brain-stimulation-0601), (Jun. 1, 2017), 3 pages.
(Continued)

*Primary Examiner* — Mark Bockelman
(74) *Attorney, Agent, or Firm* — TraskBritt

(57) ABSTRACT

A skin regeneration therapy combining precise bioelectric signals, light, and biologics for skin treatment and regeneration. Precise bioelectric signals give clear instructions to the stimulated cell DNA/RNA to produce specific regenerative proteins on demand. Bioelectric signals give clear instructions to cell membranes on what to let in and what to let out and serve as an equivalent or surrogate of environmental stimuli to cause a cell action in response.

21 Claims, 14 Drawing Sheets

Related U.S. Application Data application No. 15/460,129, filed on Mar. 15, 2017, now Pat. No. 10,646,644.

(60) Provisional application No. 62/454,521, filed on Feb. 3, 2017, provisional application No. 62/385,124, filed on Sep. 8, 2016, provisional application No. 62/375,271, filed on Aug. 15, 2016, provisional application No. 62/364,472, filed on Jul. 20, 2016, provisional application No. 62/363,012, filed on Jul. 15, 2016, provisional application No. 62/352,930, filed on Jun. 21, 2016, provisional application No. 62/308,702, filed on Mar. 15, 2016.

(51) Int. Cl.

| | | |
|---|---|---|
| *A61N 5/06* | (2006.01) | |
| *A61M 37/00* | (2006.01) | |
| *A61K 8/98* | (2006.01) | |
| *A61Q 19/08* | (2006.01) | |
| *A61M 39/02* | (2006.01) | |
| *A61N 5/067* | (2006.01) | |
| *A61N 1/362* | (2006.01) | |
| *A61N 1/36* | (2006.01) | |
| *A61N 1/372* | (2006.01) | |
| *A61M 5/142* | (2006.01) | |
| *A61M 39/00* | (2006.01) | |

(52) U.S. Cl.
CPC .... *A61M 37/0015* (2013.01); *A61M 39/0208* (2013.01); *A61N 1/326* (2013.01); *A61N 1/327* (2013.01); *A61N 5/0616* (2013.01); *A61Q 19/08* (2013.01); *A61H 2201/10* (2013.01); *A61K 2800/83* (2013.01); *A61M 5/14276* (2013.01); *A61M 2037/0023* (2013.01); *A61M 2037/0061* (2013.01); *A61M 2039/0036* (2013.01); *A61M 2202/0494* (2013.01); *A61M 2202/07* (2013.01); *A61M 2202/09* (2013.01); *A61M 2205/05* (2013.01); *A61M 2205/50* (2013.01); *A61M 2205/502* (2013.01); *A61N 1/36002* (2017.08); *A61N 1/3629* (2017.08); *A61N 1/37205* (2013.01); *A61N 2005/067* (2013.01); *A61N 2005/0647* (2013.01); *A61N 2005/0648* (2013.01); *A61N 2005/0652* (2013.01)

(58) Field of Classification Search
CPC .......... A61K 2800/83; A61M 39/0208; A61M 37/0015; A61M 2205/502; A61M 2205/50; A61M 2037/0061; A61M 5/14276; A61M 2039/0036; A61M 2205/05; A61M 2202/09; A61M 2037/0023; A61M 2202/0494; A61M 2202/07; A61M 35/30; A61H 39/002; A61H 2201/10; A61Q 19/08
See application file for complete search history.

(56) References Cited

U.S. PATENT DOCUMENTS

| | | |
|---|---|---|
| 5,211,622 A | 5/1993 | Liboff et al. |
| 5,543,318 A | 8/1996 | Smith et al. |
| 5,693,029 A | 12/1997 | Leonhardt |
| 5,713,917 A | 2/1998 | Leonhardt et al. |
| 5,725,377 A | 3/1998 | Lemler et al. |
| 5,817,139 A | 10/1998 | Kasano |
| 5,957,949 A | 9/1999 | Leonhardt et al. |
| 6,344,052 B1 | 2/2002 | Greenan et al. |
| 6,618,625 B2 | 9/2003 | Silverstone |
| 6,957,106 B2 | 10/2005 | Schuler et al. |
| 6,988,004 B2 | 1/2006 | Kanno et al. |
| 7,029,276 B2 | 4/2006 | Mao |
| 7,136,699 B2 | 11/2006 | Palti |
| 7,341,062 B2 | 3/2008 | Chachques et al. |
| 7,483,749 B2 | 1/2009 | Leonhardt et al. |
| 7,686,799 B2 | 3/2010 | Leonhardt et al. |
| 7,881,784 B2 | 2/2011 | Pasricha et al. |
| 8,133,267 B2 | 3/2012 | Leonhardt et al. |
| 8,226,407 B2 | 7/2012 | Hanewinkel et al. |
| 8,465,533 B2 | 6/2013 | Palti |
| 8,639,361 B2 | 1/2014 | Nathanson |
| 8,656,930 B2 | 2/2014 | Schuler et al. |
| 8,660,669 B2 | 2/2014 | Nemeh et al. |
| 8,738,144 B2 | 5/2014 | Schneider |
| 8,909,346 B2 | 12/2014 | Chalmers |
| 8,945,104 B2 | 2/2015 | Boone et al. |
| 9,032,964 B2 | 5/2015 | Schuler et al. |
| 9,533,170 B2 | 1/2017 | Dye et al. |
| 9,656,096 B2 | 5/2017 | Pilla |
| 9,662,184 B2 | 5/2017 | Lowe |
| 2003/0032998 A1 | 2/2003 | Altman |
| 2003/0220556 A1 | 11/2003 | Porat et al. |
| 2004/0010231 A1 | 1/2004 | Leonhardt et al. |
| 2004/0115587 A1 | 6/2004 | Breining et al. |
| 2004/0147906 A1 | 7/2004 | Voyiazis et al. |
| 2004/0236238 A1 | 11/2004 | Schuler et al. |
| 2005/0171578 A1 | 8/2005 | Leonhardt |
| 2006/0030908 A1 | 2/2006 | Powell et al. |
| 2006/0100553 A1 | 5/2006 | Lodin |
| 2007/0167984 A1 | 7/2007 | Kieval et al. |
| 2007/0190028 A1 | 8/2007 | Qu et al. |
| 2007/0265680 A1 | 11/2007 | Liu et al. |
| 2008/0227046 A1 | 9/2008 | Lowe et al. |
| 2010/0082027 A1 | 4/2010 | Chalmers |
| 2010/0184183 A1 | 7/2010 | Schussler et al. |
| 2012/0156648 A1 | 6/2012 | Kaufman et al. |
| 2013/0253413 A1 | 9/2013 | Levine et al. |
| 2014/0023983 A1 | 1/2014 | Lowe et al. |
| 2014/0214115 A1 | 7/2014 | Greiner et al. |
| 2014/0214116 A1 | 7/2014 | Peterson et al. |
| 2014/0214124 A1 | 7/2014 | Greiner et al. |
| 2014/0214144 A1 | 7/2014 | Peterson et al. |
| 2017/0028184 A1 | 2/2017 | Godden et al. |
| 2017/0266371 A1 | 9/2017 | Leonhardt et al. |
| 2017/0274206 A1 | 9/2017 | Leonhardt |
| 2018/0064935 A1 | 3/2018 | Leonhardt et al. |
| 2019/0015661 A1 | 1/2019 | Leonhardt et al. |
| 2019/0022389 A1 | 1/2019 | Leonhardt |
| 2019/0022396 A1 | 1/2019 | Leonhardt |

FOREIGN PATENT DOCUMENTS

| | | |
|---|---|---|
| JP | 2013-034881 A | 2/2013 |
| KR | 10-0726825 B1 | 6/2007 |
| WO | 92/17118 A1 | 10/1992 |
| WO | 2006/116728 A2 | 11/2006 |
| WO | 2007/146187 A2 | 12/2007 |
| WO | 2008/145724 A1 | 12/2008 |
| WO | 2009/021535 A1 | 2/2009 |

OTHER PUBLICATIONS

Aydin et al., "Focusing of Electromagnetic Waves by a Left-Handed Metamaterial Flat Lens," vol. 13, (2005), pp. 8753-8759.

Barker et al., "A Formidable Foe is Sabotaging Your Results: What You Should Know About Biofilms and Wound Healing," Plastic and Reconstructive Surgery, vol. 139, (2017), pp. 1184e-1194e.

Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.

Borden et al., "Electric Current-Induced Detachment of *Staphylococcus epidermidis* Biofilms from Surgical Stainless Steel," Applied and Environmental Microbiology, vol. 70, (2004), pp. 6871-6874.

Cai et al., "Intermedin Inhibits Vascular Calcification by Increasing the Level of Matrix (Gamma)-Carboxyglutamic Acid Protein," Cardiovascular Research, vol. 85, (2010), pp. 864-873.

(56) References Cited

OTHER PUBLICATIONS

Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.

Caubet et al., "A Radio Frequency Electric Current Enhances Antibiotic Efficacy Against Bacterial Biofilms," Antimicrobial Agents and Chemotherapy, vol. 48, (2004), vol. 4662-4664.

Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.

Chen et al., "The Role and Mechanism of (Alpha)-Klotho in the Calcification of Rat Aortic Vascular Smooth Muscle Cells," BioMed Research International, vol. 2015, (2015), 7 pages.

Chen et al., "The Strategy to Prevent and Regress the Vascular Calcification in Dialysis Patients," BioMed Research International, vol. 2017, (2017), 11 pages.

Chiang et al., "Silver-Palladium Surfaces Inhibit Biofilm Formation," Applied and Environmental Microbiology, vol. 75, (2009), pp. 1674-1678.

Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.

Costerton et al., "The Application of Biofilm Science to the Study and Control of Chronic Bacterial Infections," The Journal of Clinical Investigation, vol. 112, (2003), pp. 1466-1477.

Delcaru et al., "Microbial Biofilms in Urinary Tract Infections and Prostatitis: Etiology, Pathogenicity, and Combating strategies," Pathogens, vol. 5, (2016), 12 pages.

Ehrlich et al., "Engineering Approaches for the Detection and Control of Orthopaedic Biofilm Infections," Clinical Orthopaedics and Related Research, vol. 437, (2005), pp. 59-66.

Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.

Giladi et al., "Microbial Growth Inhibition by Alternating Electric Fields," Antimicrobial Agents and Chemotherapy, vol. 52, (2008), pp. 3517-3522.

Golberg et al., "Eradication of Multidrug-Resistant A. Baumannii in Burn Wounds by Antiseptic Pulsed Electric Field," Technology, vol. 2, (2014), pp. 153-160.

Golberg et al., "Pulsed Electric Fields for Burn Wound Disinfection in a Murine Model," Journal of Burn Care & Research, vol. 36, (2015), pp. 7-13.

Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.

Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.

Hleonhardt, Leonhardt Announces Vibrational Energy Device for Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.

https://www.dicardiology.com/content/bioleonhardt-unveils-stem-pump Jan. 28, 2014.

Istanbullu et al., "Electrochemical Biofilm Control: Mechanism of Action," Biofouling, vol. 28, (2012), pp. 769-778.

Kasimanickam et al., "Prevention and Treatment of Biofilms by Hybrid- and Nanotechnologies," International journal of Nanomedicine, vol. 8, (2013), pp. 2809-2819.

Kim et al., "Effect of Electrical Energy on the Efficacy of Biofilm Treatment Using the Bioelectric Effect," NPJ Biofilms and Microbiomes, vol. 1, (2015), Article 15016, 8 pages.

Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.

Lasserre et al., "Influence of Low Direct Electric Currents and Chlorhexidine Upon Human Dental Biofilms," Clinical and Experimental Dental Research, vol. 2, (Jul. 2016), pp. 146-154.

Lasserre et al., "Oral Microbes, Biofilms and Their Role in Periodontal and Peri-Implant Diseases," Materials, vol. 11, (Sep. 2018), Article 1802, 17 pages.

Lee et al. "Hepatocyte growth factor (HGF) activator expressed in hair follicles is involved in in vitro HGF-dependent hair follicle elongation," J. Dermatol. Sci., 25(2):156-63 (Feb. 2001).

Lee et al., "Targeted Release of Tobramycin From a pH-Responsive Grafted Bilayer Challenged With *S. aureus*," Biomacromolecules, vol. 16, (2015), pp. 650-659.

Lei et al., "Efficacy of Reversal of Aortic Calcification by Chelating Agents," Calcified Tissue International, vol. 93, (Nov. 2013), 15 pages.

Leibrock et al., "NH4Cl Treatment Prevents Tissue Calcification in Klotho Deficiency," Journal of the American Society of Nephrology, vol. 26, (2015), pp. 2423-2433.

Li, et al. "Local injection of RANKL facilitates tooth movement and alveolar bone remodelling." Oral Diseases, 25(2), 550-560. https://doi.org/10.1111/odi.13013.

Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.

McLean et al., "Training the Biofilm Generation—a Tribute to J. W. Costerton," Journal of Bacteriology, vol. 194, (Dec. 2012), pp. 6706-6711.

Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).

Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.

Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.

Novickij et al., "Induction of Different Sensitization Patterns of MRSA to Antibiotics Using Electroporation," Molecules, vol. 23,(2018), Article 1799, 10 pages.

O'Neill et al., "Recent Progress in the Treatment of Vascular Calcification," Kidney International, vol. 78, (Dec. 2010), pp. 1232-1239.

Palza et al., "Electroactive Smart Polymers for Biomedical Applications," Materials, vol. 12, (2019), 24 pages.

Plumbingtoday, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.

Pozo et al., "Bioelectric Effect and Bacterial Biofilms. A Systematic Review," The International Journal of Artificial Organs, vol. 31, (2008), pp. 786-795.

Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35-40.

Pozo et al., "Prevention of *Staphylococcus epidermidis* Biofilm Formation Using Electrical Current," Journal of Applied Biomaterials & Functional Materials, vol. 12, (2014), pp. 81-83.

Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.

(56) References Cited

OTHER PUBLICATIONS

Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Roy et al., "Disposable Patterned Electroceutical Dressing (PED-10) Is Safe for Treatment of Open Clinical Chronic Wounds," Advances in Wound Care, vol. 8, (1019), pp. 149-159.
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4 (3):312-5 (Dec. 1999).
Yamaguchi, "RANK/RANKL/OPG during orthodontic tooth movement", Orthod Craniofac Res. May 2009; 12(2):113-9. doi: 10.1111/j.1601-6343.2009.01444.x.
What Is Elastin? http://www.keracyte.com/index.php/site/page?view=whatIsElastin.
Wei et al., "Epicardial FSTL1 reconstitution regenerates the adult mammalian heart," Nature 525: 479-485 (Sep. 24, 2015).
Walsh & Choi "Biology of the RANK* RAN* OPG System in Immunity, Bone, and Beyond", Front Immunol. 2014; 5: 511.
W. Hoffmann, "Regeneration of the gastric mucosa and its glands from stem cells", Curr Med Chem, 15(29):3133-44 (2008).
Stenn et al., "Bioengineering the Hair Follicle," Organogenesis, 3(1): 6-13 (Jan.-Mar. 2007).
Spadari et al., Electrical stimulation enhances tissue reorganization during orthodontic tooth movement in rats; Clinical Oral Investigations, Jan. 2017, vol. 21, Issue 1, pp. 111-120, Abstract.
Signature Orthodontics "Accelerated Tooth Movement", http://www.sigortho.com/accelerated-tooth-movement, visited Mar. 15, 2017.
Seifi & Jeszri "Correlation of bone resorption induced by orthodontic tooth movement and expression of RANKL in rats", Dental Journal, vol. 26, No. 4 (2009).
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Robert Ferris, "Battle against baldness turns to stem cells" http://www.cnbc.com/2015/01/29/studies-indicate-its-possible-to-use-stem-cells-to-cure-baldness.html (Jan. 29, 2015).
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).
R. Hamman "Modulation of RANKL and Osteoprotegerin in Adolescents Using Orthodontic Forces", Masters Thesis, University of Tennessee (2010).
Prochazka et al., "Cocktail of Factors from Fat-derived Stem Cells Shows Promise for Critical Limb Ischemia" http://www.sciencenewsline.com/news/2016012204520017.html (Jan. 21, 2016).
P. Banerjee "Electrical muscle stimulation for chronic heart failure: an alternative tool for exercise training?" Curr Heart Fail Rep., 7(2):52-8. doi: 10.1007/s11897-010-0013-9 (Jun. 2010).
Our Approach to Improve Hair Loss by Increasing Hair Growth Factor IGF-1, http://www.jhgc.com.sg/theory/igf-1/index.html.
Otero et al. "Expression and Presence of OPG and RANKL mRNA and Protein in Human Periodontal Ligament with Orthodontic Force", Gene-Regulation-and-Systems-Biology, 2016, 10, 15-20.
Nimeri et al. "Acceleration of tooth movement during orthodontic treatment—a frontier in Orthodontics", Prog Orthod 2013; 14:42; DOI: 10.1186/2196-1042-14-42.
Medtronic "Cardiac Resynchronization Therapy (CRT) Devices for Heart Failure", http://www.medtronic.com/us-en/patients/treatments-therapies/crt-devices.html
Marie Ellis, "Cure for baldness? Stem cells bring hope" http://www.medicalnewstoday.com/articles/271898.php.

Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Kim et al., The effects of electrical current from a micro-electrical device on tooth movement, http://e-kjo.org/search.php?where=aview&id=10.4041/kjod.2008.38.5.337& . . . visited Aug. 2, 2017.
Khan et al. "Accelerating Tooth Movement: What Options We Have?" J Dent Health Oral Disord Ther 2016, 5(7): 00181.
Keles et al. "Inhibition of tooth movement by osteoprotegerin vs. pamidronate under conditions of constant orthodontic force", Eur J Oral Sci. Apr. 2007;115(2):131-6.
Kaur et al. "Electrically conductive polymers and composites for biomedical applications", RSC Adv., 2015,5, 37553-37567 DOI: 10.1039/C5RA01851J.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kanzaki et al. "Local RANKL gene transfer to the periodontal tissue accelerates orthodontic tooth movement", Gene Therapy, (2006) 13, 678-685.
Kanzaki et al. "Local OPG gene transfer to periodontal tissue inhibits orthodontic tooth movement." J Dent Res 2004;83:92/ 925.
Kanno et al., Establishment of a Simple and Practical Procedure Applicable to Therapeutic Angiogenesis, Circulation, 1999, pp. 2682-2687, vol. 99.
K. Hart, Katherine A.nn D.D.S., "RANKL and Osteoprotegerin Levels in Response to Orthodontic Forces" (2012). Theses and Dissertations (ETD). Paper 107. http://dx.doi.org/10.21007/etd.cghs.2012.0127.
Jia et al., "Activin B Promotes Initiation and Development of Hair Follicles in Mice" Cells Tissues Organs, 198:318-326 (Feb. 2014).
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Israeli innovation uses nerve stimulation to treat heart failure https://www.israel21c.org/israeli-innovation-uses-nerve-stimulation-to-treat-heart-failure/ (Feb. 11, 2007).
Involvement of hepatocyte growth factor/scatter factor and Met receptor signaling in hair follicle morphogenesis and cycling, FASEB J Feb. 2000 14:319-332.
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
Hy et al., "Insulin-like growth factor 1 and hair growth," Dermatol Online J,; 5(2):1 (Nov. 1999).
Hu Klein, "Vagus Nerve Stimulation: A new approach to reduce heart failure" Cardiology Journal (2010).
Holding et al. "The correlation of RANK, RANKL and TNFa expression with bone loss volume and polyethylene wear debris around hip implants" Biomaterials 27(30):5212-9—Nov. 2006.
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Hearts build new muscle with this simple protein patch, jacobsschool.ucsd.edu/news/news_ releases/release.sfe?id=1813 (Sep. 16, 2015).
Hair Growth Factors, Nanogen, http://www.svijet-kose.com/dokumenti/Serum-vegf.pdf.
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26 (4):671-80.
Fukuoka et al., "The Latest Advance in Hair Regeneration Therapy Using Proteins Secreted by Adipose-Derived Stem Cells" The American Journal of Cosmetic Surgery, 29(4):273-282 (2012).
Fukuoka and Suga, "Hair Regeneration Treatment Using Adipose-Derived Stem Cell Conditioned Medium: Follow-up With Trichograms" Eplasty, 15:e10 (Mar. 2015).
Electrical brain stimulation could support stroke recovery https://www.sciencedaily.com/releases/2016/03/160316151108.htm (Mar. 16, 2016).

(56) References Cited

OTHER PUBLICATIONS

Electric Tumor Treatment Fields, No. 0827 Policy, http://www.aetna.com/cpb/medical/data/800 _899/0827.html (Nov. 18, 2016).
Elastatropin(Registered) in Scalp & Hair Conditioning https://www.proteingenomics.com/haircare.html.
Dong-Hwan Kim et al., The effects of electrical current from a micro-electrical device on tooth movement, Korean Orthod., Oct. 2008, 38(5):337-346.
Dibart et al. "Tissue response during Piezocision-assisted tooth movement: a histological study in rats", Eur J Orthod (2014) 36 (4): 457-464; DOI: https://doi.org/10.1093/ejo/cjt079.
Control of pelage hair follicle development and cycling by complex interactions between follistatin and activin, FASEB J (Jan. 2, 2003).
Control of Hair Growth by a Growth Factor Protein, http://www.hairloss-reversible.com/control-of-hair-growth-by-a-growth-factor-protein/.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chang et al. Effect of Pulse-Burst Electromagnetic Field Stimulation on Osteoblast Cell Activities; Bioelectromagnetics 25:457-465 (2004).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Blood Vessels Hold Key to Thicker Hair Growth, https://www.sciencedaily.com/releases/2001/02/010215074636.htm(Feb. 2001).
Bio-Leonhardt "Micro Stimulator" http://www.bioleonhardt.com/micro-stimulator/.
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
Almpani et al., "Nonsurgical Methods for the Acceleration of the Orthodontic Tooth Movement", Tooth Movement. Fronl Oral Biol., vol. 18, pp. 80-91 (Karger, Basel, CH 2016) (DOI:10.1159/000382048), Published online: Nov. 24, 2015.
Alice Park, "Shrinking Stem Cells Are the Real Reason for Hair Loss" Time, (Feb. 5, 2016).
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.
Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.
Scott Jeffrey, "How to Decalcify Your Pineal Gland (and Why It's Really Important for Higher Mental Performance)," (available at https://scottjeffrey.com/decalcify-your-pineal-gland/), Retrieved on May 23, 2019, 23 pages.
Shahid et al., "Rhinosinusitis in Children," ISRN Otolaryngology, vol. 2012, Article ID 851831, (Dec. 2012), 11 pages.
Sharon M Moe, "Klotho: A Master Regulator of Cardiovascular Disease?," Circulation, vol. 125, (2012), pp. 2181-2183.
Shirtliff et al., "Assessment of the Ability of the Bioelectric Effect to Eliminate Mixed-Species Biofilms," Applied and Environmental Microbiology, vol. 71, (2005), pp. 6379-6382.
Shoji-Matsunaga et al. "Osteocyte regulation of orthodontic force-mediated tooth movement via RANKL expression." Scientific Reports, 7: 8753, published online Aug. 18, 2017 DOI:10.1038/s41598-017-09326-7.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative *Staphylococci* on Activities of Various Antimicrobial Agents," Antimicrobial Agents and Chemotherapy, vol. 42, (Apr. 1998), pp. 939-941.
Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.
Stoodley et al., "Influence of Electric Fields and pH on Biofilm Structure as Related to the Bioelectric Effect," Antimicrobial Agents and Chemotherapy, vol. 41, (1997), pp. 1876-1879.
Sultana et al., "Electrochemical Biofilm Control: A Review," Biofouling, vol. 31, (2015), pp. 745-758.
Szkotak et al., "Differential Gene Expression to Investigate the Effects of Low-Level Electrochemical Currents on Bacillus subtilis," AMB Express, vol. 1, (Nov. 2011), 12 pages.
Vinod Krishnan, Ze'ev Davidovitch (eds.), Biological Mechanisms of Tooth Movement, (John Wiley & Sons 2015 (10 Pages).
Wang et al., "Controlling *Streptococcus mutans* and *Staphylococcus aureus* Biofilms With Direct Current and Chlorhexidine," AMB Express, vol. 7, (Nov. 2017), 9 pages.
Wellman et al., "Bacterial Biofilms and the Bioelectric Effect," Antimicrobial Agents and Chemotherapy, vol. 40, (1996), pp. 2012-2014.
Wong et al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.
Wu et al., "Vascular Calcification: an Update on Mechanisms and Challenges in Treatment," Calcified Tissue International, vol. 93, (Oct. 2013), pp. 365-373.
Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.
Yarbrough et al., "Specific Binding and Mineralization of Calcified Surfaces by Small Peptides," Calcified Tissue International, vol. 86, (2010), pp. 58-66.
Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.
Zhang et al., "Highly Stable and Reusable Imprinted Artificial Antibody Used for in Situ Detection and Disinfection of Pathogens," Chemical Science, vol. 6, (2015), pp. 2822-2826.
Showkatbakhsh et al. "The effect of pulsed electromagnetic fields on the acceleration of tooth movement." World J Orthod. 2010 Winter;11(4):e52-6.
Sisay et al. "The RANK/RANKL/OPG system in tumorigenesis and metastasis of cancer stem cell: potential targets for anticancer therapy" Onco Targets Ther. 2017; 10: 3801-3810.
Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009.07.115. Epub Jul. 28, 2009.
Tan et al. "Bioelectric Perturbations in Orthodontic tooth movement" 2010 Journal of Dental Sciences & Research 1:1: pp. 41-49.
Tavlasoglu et al. "Is partial decalcification of posterior mitral annular bed logical in all mitral valve replacement procedures?" European Journal of Cardio-Thoracic Surgery 43 (2013) 449-450.
Tokyo Medical and Dental University "RANKL expressed by osteocytes has an important role in orthodontic tooth movement" Science Daily Oct. 20, 2017.
Totsugawa, et al. "Ultrasonic annular debridement in minimally invasive aortic valve replacement" Gen Thorac Cardiovasc Surg. Jan. 2020;68(1):81-83. doi: 10.1007/s11748-019-01158-8. Epub Jun. 15, 2019. (Abstract Only).
Valvublator Heart Valve Regeneration, accessed Apr. 24, 2020 https://valvublator.com (6 pages).

(56) References Cited

OTHER PUBLICATIONS

Van Dam et al. "RANK/RANKL signaling inhibition may improve the effectiveness of checkpoint blockade in cancer treatment" Critical Reviews in Oncology/Hematology vol. 133, Jan. 2019, pp. 85-91.

Verna et al. "The rate and the type of orthodontic tooth movement is influenced by bone turnover in a rat model" European Journal of Orthodontics 22 (2000) 343-352.

Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/s41551-017-0157-y.

Yang "Effect RANKL Produced by Periodontal Ligament Cells on Orthodontic Tooth Movement" (2016) Dental Theses. Paper 13.

Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.

Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).

Zhao et al. "Local osteoprotegerin gene transfer inhibits relapse of orthodontic tooth movement." Am J Orthod Dentofacial Orthop. Jan. 2012; 141(1)30-40. doi: 10.1016/j.ajodo.2011.06.035.

Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.

Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.

Schardong et al., "Intradialytic neuromuscular electrical stimulation reduces DNA damage in chronic kidney failure patients: a randomized controlled trial," Biomarkers, vol. 23, Issue 5, 2018, pp. 1-11.

Niiranen et al., "Relative Contributions of Arterial Stiffness and Hypertension to Cardiovascular Disease: The Framingham Heart Study," Journal of the American Heart Association, vol. 5, No. 11, 2016, 8 pages.

Leonhardt's Launchpads Announces Filing of Patent for Bioelectric Stimulation Controlled Klotho Expression—Powerful Anti-aging and Regeneration Promoting Protein, by API Podder, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.

Abstract of Zhang et al., "Comparison of arterial stiffness in non-hypertensive and hypertensive population of various age groups," Jan. 24, 2018, 2 pages.

Abstract of Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages.

Abstract of Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830 >, 1 page.

Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.

Bang et al., "Attenuation of Hypertension by C-Fiber Stimulation of the Human Median Nerve and the Concept-Based Novel Device," Scientific Reports, vol. 8, (2018), 12 pages.

Beitelshees et al. "CXCL5 polymorphisms are associated with variable blood pressure in cardiovascular disease-free adults" Hum Genomics. 2012; 6(1): 9.

Chen et al., Efficacy and Safety of Acupuncture for Essential Hypertension: A Meta-Analysis, Medical Science Monitor, vol. 24, (2018), pp. 2946-2969.

Cowburn et al. "HIF isoforms in the skin differentially regulate systemic arterial pressure" Proc Natl Acad Sci U S A. Oct. 22, 2013; 110(43): 17570-17575.

Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.

Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.

Flachskampf et al., "Randomized Trial of Acupuncture to Lower Blood Pressure," Circulation, vol. 115, (2007), pp. 3121-3129.

Greenwald "Pulse pressure and arterial elasticity" QJM: An International Journal of Medicine, vol. 95, Issue 2, 2002, pp. 107-112.

Healthcmi, "Acupuncture Combats Hypertension in University of California Research," Available online at < https://www.healthcmi.com/Acupuncture-Continuing-Education-News/1688-acupuncture-c . . . >, (2016), 9 pages.

Healthcmi, "Acupuncture Controls Hypertension in Groundbreaking Trial," Available online at < https://www.healthcmi.com/Acupuncture-Continuing-Education-News/1804-acupuncture-c . . . >, (2017), 9 pages.

Healthcmi, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.

Leonhardt "Leonhardt Adds HIF-1 Alpha to Estate of Bioelectric Controlled Release Regenerative Proteins" Press Release, Published Jun. 13, 2017.

Li "Regulation of Renal Oxygenation and Blood Pressure" Art. Virginia Commonwealth University, Richmond, VA, United States (Abstract).

Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.

Li et al., "Repetitive Electroacupuncture Attenuates Cold-Induced Hypertension through Enkephalin in the Rostral Ventral Lateral Medulla," Scientific Reports, vol. 6, (2016), 10 pages.

Li et al., "The Mechanism of Acupuncture in Treating Essential Hypertension: A Narrative Review," International Journal of Hypertension, vol. 2019, (2019), Article ID 8676490, 10 pages.

Longhurst et al. "Evidence-based blood pressure reducing actions of electroacupuncture: mechanisms and clinical application" Sheng Li Xue Bao. Oct. 25, 2017; 69(5): 587-597.

Nordstorm "Electrical Stimulation Blood Pressure Treatment Devices Market to Set Astonishing Growth by 2026" Art. Apr. 4, 2019 Gator Ledger.

Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.

Sethi et al. "Aortic stiffness: pathophysiology, clinical implications, and approach to treatment" Integr Blood Press Control. 2014; 7: 29-34.

Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.

Tan et al., "Acupuncture Therapy for Essential Hypertension: a Network Meta-Analysis," Annals of Translational Medicine, vol. 7, (2019), pp. 1-12.

UCIrvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.

Vilela-Martin et al., "Effects of Transcutaneous Electrical Nerve Stimulation (TENS) on Arterial Stiffness and Blood Pressure in

(56) References Cited

OTHER PUBLICATIONS

Resistant Hypertensive Individuals: Study Protocol for a Randomized Controlled Trial," Trials, vol. 17, (2016), pp. 1-13.
Warner "Inflammation Adds to Blood Pressure Risks, High Blood Pressure and C-Reactive Protein May Trigger Heart Attack, Stroke" Art WebMD Health News (2003) 2 pages.
Welch "RGS2 Proteins Regulate Blood Pressure" JASN Nov. 2010, 21 (11) 1809-1810.
Yang et al., "Acupuncture for hypertension," Cochrane Database of Systematic Reviews, Available Online at < https://www.cochranelibrary.com/cdsr/doi/10.1002/14651858.CD008821.pub2/full >, (2018), 4 pages.
Yu et al. "Association between inflammation and systolic blood pressure in RA compared to patients without RA" Arthritis Research & Therapy vol. 20, Article No. 107 (2018).
Ando et al. "RANKL/RANK/OPG: key therapeutic target in bone oncology" Curr Drug Discov Technol. Sep. 2008; 5(3): 263-268.
Atkinson et al. "Bioelectric Properties of the Tooth" 1969 vol. 48 issue: 5, pp. 789-794.
Aubert et al. "A new ultrasonic process for a renewal of aortic valve decalcification" Cardiovascular Ultrasound 2006, 4:2 doi:10.1186/1476-7120-4-2.
Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 | vol. 5 | Article 196.
Bi et al. "Key Triggers of Osteoclast-Related Diseases and Available Strategies for Targeted Therapies: A Review" Front Med (Lausanne). 2017; 4: 234. doi: 0.3389/fmed.2017.00234.
Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11Imaging and Bioengineering, Dec. 17, 2015).
Brooks et al. "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.
Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.
Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA.117.10560.) Downloaded from http://ahajournals.org by on Apr. 24, 2020 (9 pages).
Christouls et al. "Pathogenesis and Management of Myeloma Bone Disease" Expert Rev Hematol. 2009; 2(4):385-398.
Collins "Bioelectric Signals Can Be Used to Detect Early Cancer," Tufts News, http://now.tufts.edu/news-releases/bioelectric-signals-used-detect-early-cancer (Feb. 1, 2013).
Dietrich et al. "Decalcification of the mitral annulus: surgical experience in 81 patients" Thorac Cardiovasc Surg. Oct. 2006;54(7):464-7 (Abstract Only).
El-Bialy et al. "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.
Fatemi et al. "Imaging elastic properties of biological tissues by low-frequency harmonic vibration" Proceedings of the IEEE, 91(10):1503-1519 (Oct. 2003).
Fili et al. "Therapeutic implications of osteoprotegerin" Cancer Cell International vol. 9, Article No. 26 (2009).
Fonseca et al. "Electrical stimulation: Complementary therapy to improve the performance of grafts in bone defects?" Journal of Biomedical Materials Research Part B: Applied Biomaterials 2018 vol. 000b, Issue 0.

Goranov et al. "Bone Lesions in Multiple Myeloma—The OPG/RANK-ligand System" Folia Med (Plovdiv). 2004; 46(3): 5-11 (Abstract Only).
Goswami et al. "Osteoprotegerin rich tumor microenvironment: implications in breast cancer" Oncotarget. Jul. 5, 2016; 7(27): 42777-42791.
Guimarães-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.
Gurbax et al. "Accelerated Orthodontic Tooth Movement: A Review" mod Res Dent. 1(2). MRD.000508. 2017. DOI: 10.31031/MRD.2017.01.000508.
Heart Valve Calcifications-Focused Ultrasound TherapyFocused Ultrasound Therapy; Research Paper Last Updated: Jan. 28, 2020, the Focused Ultrasound Foundation Newsletter (5 pages).
Holen et al. "Role of Osteoprotegerin (OPG) in Cancer" Clin Sci (Lond). Mar. 2006; 110(3):279-91. doi: 10.1042/CS20050175.
Hu et al. "Klotho Deficiency Causes Vascular Calcification in Chronic Kidney Disease" J Am Soc Nephrol. Jan. 2011; 22(1): 124-136.
Hu et al. "Exosomes derived from human adipose mesenchymal stem cells accelerates cutaneous wound healing via optimizing the characteristics of fibroblasts", Nature Scientific Reports, vol. 6, Article No. 32993 (2016).
Huang et al. "Myocardial transfection of hypoxia-inducible factor-1α and co-transplantation of mesenchymal stem cells enhance cardiac repair in rats with experimental myocardial infarction", Stem Cell Research & Therapy 5:22 (2014) DOI: 10.1186/scrt410.
Hudson et al. "Local delivery of recombinant osteoprotegerin enhances postorthodontic tooth stability" Calcif Tissue Int. Apr. 2012; 90(4):330-42. doi: 10.1007/s00223-012-9579-4.
Iglesias-Linares et al. "The use of gene therapy vs. corticotomy surgery in accelerating orthodontic tooth movement" Orthod Craniofac Res. Aug. 2011; 14(3):138-48. doi: 10.1111/j.1601-6343.2011.01519.x.
Infante et al. "RANKL/RANK/OPG system beyond bone remodeling: involvement in breast cancer and clinical perspectives" Journal of Experimental & Clinical Cancer Research (2019) 38:12. https://doi.org/10.1186/s13046-018-1001-2.
International Search Report for International Application No. PCT/US19/52288, dated Jan. 10, 2020, 11 pages.
International Written Opinion for International Application No. PCT/US19/52288, dated Jan. 10, 2020, 07 pages.
Jouybar et al. "Enhanced Skin Regeneration by Herbal Extract-Coated Poly-L-Lactic Acid Nanofibrous Scaffold" Artif Organs. Nov. 2017; 41(11):E296-E307. doi: 10.1111/aor.12926 (Abstract Only).
Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.
King et al. "Mechanical Decalcification of the Aortic Valve" 272 The Annals of Thoracic Surgery vol. 42 No. 3 Sep. 1986 (pp. 269-272).
Kondo et al. "Types of tooth movement, bodily or tipping, do not affect the displacement of the tooth's center of resistance but do affect the alveolar bone resorption" Angle Orthod Jul. 2017; 87(4):563-569.
Kose et al. "Citric acid as a decalcifying agent for the excised calcified human heart valves" Anadolu Kardiyol Derg 2008; 8: 94-8 (Eng Abstract).
Lamoureux et al. "Therapeutic Relevance of Osteoprotegerin Gene Therapy in Osteosarcoma: Blockade of the Vicious Cycle between Tumor Cell Proliferation and Bone Resorption" Cancer Res Jan. 2007 67(15):7308-7318; DOI: 10.1158/0008-5472.CAN-06-4130.
Liang et al. "Therapeutic effect of low-intensity pulsed ultrasound on temporomandibular joint injury induced by chronic sleep deprivation in rats" Am J Transl Res. 2019; 11(6): 3328-3340.
Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.

(56) References Cited

OTHER PUBLICATIONS

Martin "Historically significant events in the discovery of RANK/RANKL/OPG" World J Orthop. Oct. 18, 2013; 4(4): 186-197. doi: 10.5312/wjo.v4.i4.186.
McBride et al. "Aortic valve decalcification" J Thorac Cardiovasc Surg. Jul. 1990;100(1):36-42; discussion 42-3 (Abstract Only).
McGrath "OPG/RANKL/RANK Pathway as a Therapeutic Target in Cancer" Journal of Thoracic Oncology, Sep. 2011 6(9): 1468-1473.
Norton et al. "Bioelectric Perturbations of Bone: Research Directions and Clinical Applications" Angle Orthod (1984) 54 (1): 73-87.
Novack "Inflammatory osteoclasts, a different breed of bone eaters?" Arthritis Rheumatol. Dec. 2016; 68(12): 2834-2836. doi: 101002/art.39835.
Oranger et al. "Cellular Mechanisms of Multiple Myeloma Bone Disease" Clinical and Developmental Immunology vol. 2013, Article ID 289458, 11 pages http://dx.doi.org/10.1155/2013/289458.
Oyajobi "Multiple myeloma/hypercalcemia" Arthritis Research & Therapy vol. 9, Article No. S4 (2007).
Pierce et al. "Collection and characterization of amniotic fluid from scheduled C-section deliveries," Cell Tissue Bank, DOI 10.1007/s10561-016-9572-7 (Springer, 2012) and is available from Irvine Scientific.
Price et al. "Mitral Valve Repair is Feasible Following Extensive Decalcification and Reconstruction of the Atrioventricular Groove" J Heart Valve Dis. Jan. 2015;24(1):46-52 (Abstract Only).
Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.
Raje et al. "Role of the RANK/RANKL Pathway in Multiple Myeloma" Clin Cancer Res 2019 25(1):12-20; DOI: 10.1158/1078-0432.CCR-18-1537.
Showkatbakhsh et al. "Effect of Intra-Canal Direct Current Electric Stimulation on Orthodontic Tooth Movement: An Experimental Study in Canines" Journal of Dental School 2016; 34(3): 157-67.
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Thattaliyath et al. "Modified Skeletal Myoblast Therapy for Cardiac Failure Using AAV SDF-1," Proc. Intl. Soc. Mag. Reson. Med. 16, p. 579 (2008).
Tamaki et al. "Cardiomyocyte Formation by Skeletal Muscle-Derived Multi-Myogenic Stem Cells after Transplantation into Infarcted Myocardium," PLoS ONE 3(3): e1789. doi:10.1371/journal.pone.0001789 (Mar. 2008).
Sahoo and Losordo "Exosomes and Cardiac Repair After Myocardial Infarction," Circulation Research, 114:333-344 (Jan. 16, 2014).
Procházka et al. "Therapeutic Potential of Adipose-Derived Therapeutic Factor Concentrate for Treating Critical Limb Ischemia," Cell Transplantation, 25(9), pp. 1623-1633(11) (2016).
Park et al. "Effects of SM-215 on Hair Growth by Hair Follicle Stimulation," Indian Journal of Science and Technology, vol. 8(25), DOI: 10.17485/ijst/2015/v8i25/80263, (Oct. 2015).
Mosteiro et al. "Tissue damage and senescence provide critical signals for cellular reprogramming in vivo." Science, 2016; 354 (6315): aaf4445 DOI: 10.1126/science.aaf4445.
Mass Device "Greatbatch wins FDA PMA for Algovita SCS," http://www.massdevice.com/greatbatch-wins-fda-pma-for-algovita-scs/ (Dec. 1, 2015).
Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter-defibrillators_icds_85,P00234/, last visited Sep. 12, 2018.
D. Grady "Electrical Scalp Device Can Slow Progression of Deadly Brain Tumors," New York Times, https://www.nytimes.com/2014/11/16/health/electrical-scalp-device-can-slow-progression-of-deadly-brain-tumors.html?_r=0 (Nov. 15, 2014), last visited Sep. 12, 2018.
Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf, last visited Sep. 12, 2018.
Chernet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Bradshaw et al. "Designer self-assembling hydrogel scaffolds can impact skin cell proliferation and migration" Nature Scientific Reports, vol. 4, Article No. 6903 (2014).
B. Borgobello "FDA approves the treatment of brain tumors with electrical fields," New Atlas, http://newatlas.com/treatment-of-brain-tumors-with-electrical-fields/21433/ (Feb. 13, 2012), last visited Sep. 12, 2018.
"FDA Approves Algovita Spinal Cord Stimulation System from Greatbatch," http://www.odtmag.com/contents/view_breaking-news/2015-12-02/fda-approves-algovita-spinal-cord-stimulation-system-from-greatbatch (Dec. 2, 2015).
"Electrical brain stimulation could support stroke recovery," sciencedaily.com/releases/2016/03/160316151108.htm (Mar. 16, 2016), last visited Sep. 12, 2018.
"Electric Tumor Treatment Fields," No. 0827 Policy, aetna.com/cpb/medical/data/800_899/0827.html (Nov. 18, 2016), last visited Sep. 12, 2018.
Beebe et al. "Bioelectric Applications for Treatment of Melanoma," Cancers (Basel). Sep. 2010; 2(3): 1731-1770, published online Sep. 27, 2010; doi: 10.3390/cancers20317.
Campbell et al. "Electrical stimulation to optimize cardioprotective exosomes from cardiac stem cells" Med Hypotheses. Mar. 2016; 88:6-9. doi: 10.1016/j.mehy.215.12.022. Epub Jan. 11, 2016.
Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).
Chernet et al. "Transmembrane voltage potential is an essential cellular parameter for the detection and control of the cancer tumor development in a Xenopus model," Dis. Models and Mech. 6, pp. 595-607 (2013); Doi:10.1242/dmm.010835.
Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.
Dai et al. "Nanosecond Pulsed Electric Fields Enhance the Antitumour Effects of the mTOR Inhibitor Everolimus against Melanoma," Scientific Reports vol. 7, Article number: 39597 (2017).
Hamzelou et al. "Cancer reversed in frogs by hacking cells' electricity with light," New Scientist This Week, Mar. 16, 2016.
Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.
Keunen et al. "Anti-VEGF treatment reduces blood supply and increases tumor cell invasion in glioblastoma,"Proc. Natl. Acad. Sci. U. S. A. Mar. 1, 2011; 108(9): 3749-3754, published online Feb. 14, 2011; doi: 10.1073/pnas.1014480108.
Lanzetto et al. "Fundamental principles of an anti-VEGF treatment regimen: optimal application of intravitreal anti-vascular endothelial growth factor therapy of macular diseases," Graefes Arch. Clin. Exp. Ophthalmol. 2017; 255(7): 1259-1273 (published online May 19, 2017); doi: 10.1007/s00417-017-3647-4.
Meadows et al. "Anti-VEGF Therapies in the Clinic," Cold Spring Harb. Perspect. Med. Oct. 2, 2012(10): a006577: doi: 10.1101/cshperspect.a006577.
Mishra "Angiogenic neovessels promote tissue hypoxia," Proc. Natl. Acad. Sci. U. S. A. Sep. 20, 2016; 113(38): 10458-10460, published online Sep. 13, 2016; doi: 10.1073/pnas.1612427113.
Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from:http://www.intechopen.com/books/

(56) References Cited

OTHER PUBLICATIONS current-cancer-treatment-novel-beyond-conventional-approaches/electrotherapy-on-cancer-experiment-and-mathematical-modeling, 2011.

Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.

RFA (radiofrequency ablation), Swedish Medical Imaging, 2 pages, author unknown, undated.

Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.

FluidSync M200 micropump

Acitivin B: 6.0mV, 150Hz, pulse width 100us, square wave

EGF: 10V/cm (5V here), 500Hz, pulse width 180us, square wave

Follistatin: 10V, 50Hz, Square wave

HGF: 3.5V, 10sec burst every 30 seconds, square wave

IGF-1: 3.0mV, 22Hz, square wave

Proliferation: 15mV, 70Hz, square wave

Proliferation: 2.5-6.0V (4V here), 20Hz, pulse width 200-700us, square wave

SDF-1: 3.5mV, 30Hz, square wave

Tropoelastin: 60mV, 50Hz, square wave

VEGF: 100mV, 50Hz, square wave

SDF-1 (2nd part): 0.25mA (3.0V shown here), 100Hz, 100us pulse width, square wave

SKIN TREATMENT SYSTEM

CROSS-REFERENCE TO RELATED APPLICATIONS

This application is a continuation-in-part of U.S. patent appplication Ser. No. 15/812,760, filed on Nov. 14, 2017 and a continuation-in-part of U.S. patent appplication Ser. No. 15/460,129, filed on Mar. 15, 2017 (US 2017/0266371 A1, Sep. 21, 2017), which itself claims the benefit under 35 USC § 119 of:

U.S. Provisional Patent Application Ser. No. 62/308,702, filed Mar. 15, 2016;

U.S. Provisional Patent Application Ser. No. 62/363,012, filed Jul. 15, 2016;

U.S. Provisional Patent Application Ser. No. 62/364,472, filed Jul. 20, 2016;

U.S. Provisional Patent Application Ser. No. 62/375,271, filed Aug. 15, 2016;

U.S. Provisional Patent Application Ser. No. 62/385,124, filed Sep. 8, 2016;

U.S. Provisional Patent Application Ser. No. 62/454,521, filed Feb. 3, 2017; and U.S. Provisional Patent Application Ser. No. 62/352,930, filed Jun. 21, 2016, the disclosure of each of which is incorporated herein in its entirety by this reference.

TECHNICAL FIELD

The application relates generally to the field of cosmetic and medical devices and associated methods and treatments, and more specifically to precise bioelectrical stimulation of a subject's skin tissue, augmented with the administration of a composition comprising, among other things, stem cells and nutrients, useful to stimulate and treat the subject, the subject's skin tissue(s) and/or cells.

BACKGROUND

Various organs and tissues of the body, such as skin, lose function due to aging. Other organs and tissues suffering from loss of function have been treated with electrical current to affect a change.

For example, U.S. Pat. No. 6,988,004 to Kanno and Sato (Jan. 17, 2006), the contents of which are incorporated herein by this reference, described a method for stimulating angiogenesis. The method comprised electrically stimulating muscle below the threshold for muscle contraction and increased VEGF mRNA.

For another example, see U.S. Pat. No. 7,483,749 (Jan. 27, 2009) to Leonhardt and Chachques, the contents of which are incorporated herein by this reference, describes a method for enhancing regeneration of the myocardium. The method comprised applying electrical stimulation to an injury site in the myocardium, and could be used in combination with implantation of myogenic cells into the injury site. The electrical stimulation could be applied before or after an implantation. Also described was that a bioelectric signal could recruit stem cells to the injury site.

BRIEF SUMMARY

Described is a skin regeneration therapy. The described therapy combines precise bioelectric signals, light, and biologics for skin treatment and regeneration. Precise bioelectric signals give clear instructions to the stimulated cell DNA/RNA to produce specific regenerative proteins. Bioelectric signals give clear instructions to cell membranes on what to let in and what to let out and serve as an equivalent or surrogate of environmental stimuli to cause a cell action in response.

In certain embodiments, described is a combination of bioelectrically induced stem cell homing, together with the controlled release and/or expression of tropoelastin, and, for example, a composition of mixed biological.

In certain embodiments, described is a combination of bioelectrically induced stem cell homing, proliferation, and differentiation, and the release and/or expression of tropoelastin.

Also described is bioelectric stimulator programmed to activate release in a subject's skin of, e.g., SDF-1, IGF-1, EGF, HGF, PDGF, eNOS, VEGF, Activin A and B, A, Follistatin, IL-6, HIF-1-α, and/or tropoelastin. Described is a bioelectric stimulator including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand. Such a bioelectric stimulator preferably precisely controls release of SDF-1 in the subject, without diminishing effect over time.

Also described is a method of using the bioelectric stimulator to regenerate and/or recover a subject's skin, the method including: delivering selected electrical signals to the skin so as to precisely control protein expressions in the right sequence and volume for skin regeneration and recovery.

Such a method can further include separately delivering to the subject a cocktail of regenerative agents. A preferred biological mix composition for such use includes (1) adipose-derived stromal vascular fraction (SVF), a mixture of growth factors including SDF1, IGF-1, IGF-1, PDGF, HGF, GDF10, and/or GDF11, (2) platelet rich fibrin ("PRF") extended expression formulation, (3) amniotic fluid, (4) exosomes, (5) micro RNAs, (6) a nutrient hydrogel (e.g., LUMANAIRE™ hydrogel cream or other stem cell extract hydrogel based cream or gel), (7) alkaloids, (8) oxygenated nanoparticles, and (9) skin matrix.

Also described is a method of using the bioelectric stimulator in a subject's tissue to control release of a protein, wherein the electrical signal stimulates the production of a protein selected from the group consisting of SDF-1, IGF-1, HGF, EGF, PDGF, VEGF, HIF-1-a, eNOS, activin A, activin B, IL-6, follistatin, tropoelastin, and any combination thereof.

Also described is a method of using the bioelectric stimulator in a subject to repair DNA in the subject's skin, the method including: generating electrical signals from the bioelectric stimulator to control the release of IGF-1.

Also described is a method of using the bioelectric stimulator to achieve a desired result in a subject, wherein the desired result is skin regeneration or rejuvenation.

Also described is a bioelectric stimulator including: a power source (e.g., battery, capacitor, or other suitable source of electricity), and means for delivering an electrical signal to a subject's tissue (e.g., via electrode(s) or wirelessly), wherein the bioelectric stimulator utilizes the electrical signal to precisely control stem cell homing, proliferation and differentiation in the tissue. Such a bioelectric stimulator preferably utilizes the electrical signal to precisely control protein expression.

A preferred system includes:

1. A bioelectric stimulator that controls/stimulates the release/production of SDF-1, IGF-1, EGF, HGF, PDGF, eNOS, VEGF, Activin A and B, Follistatin, IL-6, HIF-1-a, and tropoelastin.

2. A micro infusion pump (e.g., a FLUIDSYNC™ micropump available from Fluidsynchrony of Pasadena, Calif., US), which is programmable and re-Tillable and preferably has a low cell damage design. Such a pump preferably includes a refilling silicon septum port or ports and reservoir chambers.

3. A multi-component composition that includes, for example, adipose-derived stem cells, muscle-derived stem cells (when needed for muscle), exosomes, Micro RNAs, nutrient hydrogel, growth factor cocktail, skin matrix, selected alkaloids, and/or selected anti-inflammatory agents.

The pump and stimulator may be associated with (e.g., connected to) the skin area to be treated/regenerated with a pacing infusion lead (available from Nanoscribe of Eggenstein-Leopoldshafen, Germany). The interface varies by the location of the skin, e.g., a conductive soft wrap can be used for certain applications.

The stimulator can be designed to externally deliver all regeneration promoting signals wirelessly to the subject's skin, associated tissue(s), and/or cells.

DETAILED DESCRIPTION

Figure 1:
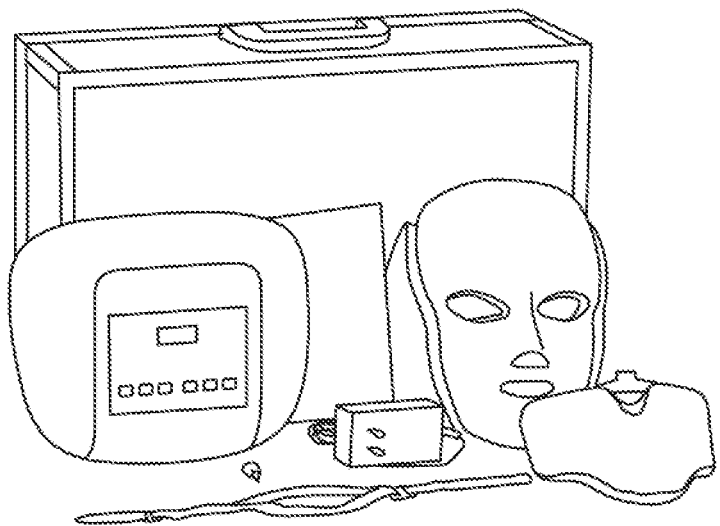
FIG. 1 depicts a programmed bioelectric stimulator together with a facemask and neck applicator. The facemask delivers bioelectric signals as well as LED light to the subject's face and neck.
Figure 2:
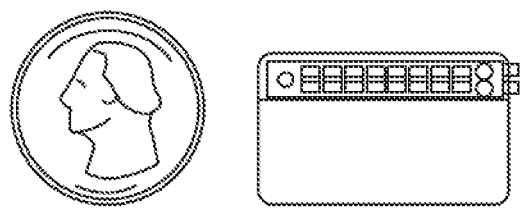
FIG. 2 depicts a programmed bioelectric stimulator depicted alongside a U.S. quarter.
Figure 3:
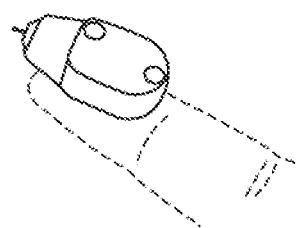
FIG. 3 depicts a micropump for use with the system.

Referring now to FIG. 1, depicted is a human use stimulator and facemask for use with treatment of a subject's face and neck. As depicted in FIG. 2, the stimulator portion may be about the size of two quarters (available from QIG Greatbatch/Greatbatch, Inc. of Frisco, Tex., US) (FIG. 2). Depicted particularly in FIG. 1 are the face and neck mask (with straps), controller/stimulator, and carrying case.

In certain embodiments, the device provides bioelectric signaling sequences applied to the subject's skin are ones for (a) SDF-1 and/or PDGF (e.g., for stem cell homing to the treated area), (b) VEGF, PDGF, HIF-1-a, CXCL5, HGF, EGF, SDF1, and/or eNOS (e.g., for growing new blood vessels in the treated area), (c) tropoelastin (e.g., to increase the elasticity of skin in the treated area), (d) follistatin (e.g., to improve muscle tone in the treated area), and (e) IGF-1 ((e.g., for DNA repair due to aging and sun damage in the treated area).

Preferably, a device provides bioelectric signaling sequences applied to the subject's skin are ones for (a) SDF-1 (stem cell homing), (b) tropoelastin (to turn back on the elasticity switch ("increase skin elasticity") that turns off at age 9 in humans), (c) IGF-1 (for DNA repair), (d) VEGF, SDF-1, HGF, EGF, PDGF, eNOS, HIF-1-a, CXCL5, tropoelastin, and/or EGF (for dermal skin repair), (e) IL's (for inflammation response/inflammation management), (f) BMP proteins, and (g) Activin A and/or B.

In certain embodiments, a device provides bioelectric signaling sequences applied to the subject's skin are signals for: (a) SDF-1 (e.g., for stem cell homing to the treated area), (b) IGF-1 ((e.g., for DNA repair due to aging and sun damage in the treated area), (c) tropoelastin (e.g., to increase the elasticity of skin in the treated area), and (d) VEGF (e.g., to improve blood circulation in the treated area). Preferably, such a device also provides bioelectric signaling sequences for application to the subject's skin for (e) PDGF, HIF-1-a, eNOS, and/or CXCL5, (e.g., to improve blood circulation in the treated area), (f) stem cell proliferation, (g) stem cell differentiation control, (h) extended PRF protein release, (i) HGF (e.g., to enhance skin regeneration), and/or (j) EGF (e.g., to aid or enhance skin regeneration).

The device may be similar in construction and form to the NUFACE® device of WO2006/116728 (Nov. 2, 2006), the contents of which are incorporated herein by this reference. The NUFACE® device comprises a hand-held housing from which a pair of electrodes project and circuitry for establishing a potential difference between the electrodes so that a microcurrent flows between the electrodes when the electrodes are placed on the skin. For other devices adaptable for use with the herein described system see, e.g., EP 0603451 A1 to Paolizzi (Jun. 29, 1994) and U.S. Pat. No. 8,639,361 to Nathanson (Jan. 28, 2014), the contents of each of which are incorporated herein by this reference. Similar devices are the LIGHTSTIM MULTIWAVE™ device for LED light therapy.

While such devices may be adapted for use herein, these prior art microcurrent devices were generally designed to accelerate healing via "current of injury" signaling, to improve mildly blood circulation and muscle tone and provide mild pain relief. For example, traditional TENS devices were designed to lower pain. Nearly all of these devices have relatively fuzzy/noisy signals compared to new modern precise bioelectric signaling stimulators, such as those used and programmed herein. Traditional microcurrent facial devices do not have specific, precise signals or sequences for controlling the release of specific regeneration promoting proteins on demand. Furthermore, even if they were programmed with these signals, they do not have the clarity of signal for the body to understand the instruction. Bioelectrical stimulators, such as those described herein, have precise programming to deliver precise clear signals to control protein expressions on demand. These controlled protein expressions are for very specific purposes.

In certain embodiments, the bioelectrical stimulation is provided by a SkinStim Model 240 High Precision Bioelectric and TENS Stimulator, which is pre-programmed for SDF-1, VEGF, IGF-1, and Tropoelastin Controlled Release. Bioelectric microcurrent and LED Face Mask (inner and outer views) such as a SkinStim Model 100 Micro-current and LED face mask may be used to treat the forehead, eyebrow, cheek, under-eye, jaw line, and jowls. Such a device preferably has, e.g., neoprene masks and straps (which are soft and oil and water resistant), a silicone outer casing of micro-current nodes and strap clasps, LED lights—rings that light up when mask is turned on, and metal nodes and wiring on inside of mask for micro-current.

Traditional microcurrent or TENS facials did not control with precision the release and/or expression of any of the above. At most, they provided a temporary, slight improvement of blood circulation. If there were however a surface wound, these general "current of injury" signals demonstrated accelerated healing.

In certain embodiments, a microcurrent and LED Mini-Mask Model 200 micro-current mini face mask is used. For applications just about the subject's eyes, a SkinStim Eye-Mask Model 100 microcurrent Eye mask may be used.

In certain embodiments, a pulsed laser light generator (e.g., one available from Epimedica of San Clemente, Calif., US) is used to provide laser light therapy to the area to be treated.

Methods and benefits of utilizing light and light emitting diodes (LEDs) for phototherapeutic treatment are described in U.S. Pat. No. 9,533,170 (Jan. 3, 2017) to Dye et al., U.S. Pat. No. 8,945,104 (Feb. 3, 2015) to Boone, III et al., and US 2006/0030908 A1 (Feb. 9, 2006) to Powell et al., the contents of each of which are incorporated herein by this reference.

Delivery may also/alternatively be through a micro-current facial conductive massage glove wherein, for example, electrodes associated with the bioelectrical stimulator are used to apply the desired electrical therapies.

Further, bioelectric signals may be used to improve muscle tone (follistatin for muscle tone improvement) and with improved muscle tone, the appearance of the overlying skin improves. Likewise, bioelectric signals may also be used to improve blood flow (VEGF, eNOS, PDGF, and HIF-1-α for blood circulation improvement). IGF-1, EGF, HGF, Activin A+B, Follistatin and PDGF are expressed via bioelectric signaling and are intended to promote skin regeneration and DNA repair.

Typical subjects to be treated are humans, and the typical areas of skin are the face, neck, arms, the back of hands, legs, etc.

Skin regeneration compositions include basic skin regeneration compositions and advanced skin regeneration compositions. A basic skin regeneration composition contains, e.g., amniotic fluid and membranes, platelet rich fibrin ("PRF") and PRF membranes, and nutrient engineered hydrogel. An advanced skin regeneration composition typically contains autologous (from patient to patient) and/or homologous stem cells (adipose-derived), ECM—matrix (skin matrix), micro RNAs, selected exosomes, selected alkaloids (e.g., tetraharmine), and oxygenated nanoparticles.

For instance, in certain embodiments, the skin regeneration composition contains bioelectric pre-treated stem cells (e.g., adipose tissue-derived), stromal fraction ("SVF"), PRF, selected growth factors, amniotic fluid, exosomes, micro RNAs in a gel, nutrient hydrogel, oxygenated nanoparticles, and skin matrix.

Stem cells may be obtained using a same-day stem cell process, which takes about 60 minutes. In such a process, first, one obtains tissue sample from the subject. Then a fat sample is processed using commercially available equipment and kits. This tissue is combined with reagent centrifuge and platelet rich fibrin ("PRF"). The stromal vascular fraction ("SVF") is washed and filtered. Stem cells are re-suspended in saline or platelet rich plasma ("PRP") and injected into the subject. The process may be repeated as needed or desired.

The stromal vascular fraction (SVF) of adipose tissue is a source of pre-adipocytes, mesenchymal stem cells (MSC), endothelial progenitor cell, T cells, B cells, mast cells as well as adipose tissue macrophages.

PRF may be provided by utilization of a SkinStim Bedside PRF Device or other platelet rich fibrin processing device.

This composition is preferably delivered repeatedly with a DermaPen™-like microneedle array over time. One such microneedle system is disclosed in US20170028184A1 to Godden et al. (Feb. 2, 2017) for a "Device and method of skin care and treatment via microneedles having inherent anode and cathode properties, with or without cosmetic or pharmacological compositions," the contents of which are incorporated herein by this reference in its entirety.

A skin matrix is a composition comprising skin cells that are to be treated. The skin matrix is believed to aid in stem cell differentiation, but in any event is found to be useful in the composition. It has been found that for the multicomponent composition, cells plus selected growth factors are better than just cells alone. See, e.g., Procházka et al. "Therapeutic Potential of Adipose-Derived Therapeutic Factor Concentrate for Treating Critical Limb Ischemia," Cell Transplantation, 25(9), pp. 1623-1633(11) (2016) and "Cocktail of Factors from Fat-derived Stem Cells Shows Promise for Critical Limb Ischemia," world wide web at sciencenewsline.com/news/2016012204520017.html (Jan. 22, 2016), the contents of each of which are incorporated herein by this reference.

Useful hydrogels (and microRNA) are known and are described in Mao et al. "13—Hydrogel fibrous scaffolds for accelerated wound healing" *Electrofluidodynamic Technologies (EFDTs) for Biomaterials and Medical Devices*, pages 251-274 (2018), Bradshaw et al. "Designer self-assembling hydrogel scaffolds can impact skin cell proliferation and migration" *Nature Scientific Reports*, vol. 4, Article number: 6903 (2014), Wang et al. "Local and sustained miRNA delivery from an injectable hydrogel promotes cardiomyocyte proliferation and functional regeneration after ischemic injury," *Nat Biomed Eng.* 2017; 1: 983-992, doi: 10.1038/s41551-017-0157-y, R. Boyle "Wound-Treating Jelly Regenerates Fresh, Scar-Free Skin", *Popular Science*, (Dec. 15, 2011), "New material developed for accelerated skin regeneration in major wounds," *Science Highlight*, (National Institute of Biomedical Imaging and Bioengineering, Dec. 17, 2015), and Jouybar et al. "Enhanced Skin Regeneration by Herbal Extract-Coated Poly-L-Lactic Acid Nanofibrous Scaffold" *Artif Organs.* 2017 November; 41(11): E296-E307. doi: 10.1111/aor.12926.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin Exosomes are formed in endosomal vesicles called multivesicular endosomes (MVEs) or multivesicular bodies, which originate by direct budding of the plasma membrane into early endosomes. The generation of exosomes to form MVEs involves the lateral segregation of cargo at the delimiting membrane of an endosome and inward budding and pinching of vesicles into the endosomal lumen. Because exosomes originate by two successive invaginations from the plasma membrane, its membrane orientation is similar to the plasma membrane. Exosomes from many cell types may contain similar surface proteins as the cell from which it is derived. Membrane proteins that are known to cluster into microdomains at the plasma membrane or at endosomes, such as tetraspanins (CD63, CD81, CD82), often are also enriched in EVs. It is also thought that endosomal sorting complex responsible for transport system and tetraspanins, which are highly enriched in MVEs, play a role in exosome production. How cytosolic constituents are recruited into exosomes is unclear but may involve the association of exosomal membrane proteins with chaperones, such as HSC70, that are found in exosomes from most cell types. MVEs are also sites of miRNA-loaded RNA-induced silencing complex accumulation, and the fact that exosome-like vesicles are considerably enriched in GW182 and AGO2 implicates the functional roles of these proteins in RNA sorting to exosomes. Exosomes are released to the extracellular fluid by fusion of MVE to the plasma membrane of a cell, resulting in bursts of exosome secretion. Several Rab GTPases such as Rab 27a and Rab27b, Rab11 and Rab35, all seem to be involved in exosomes release.

Useful exosomes are known and described in Hu et al. "Exosomes derived from human adipose mesenchymal stem cells accelerates cutaneous wound healing via optimizing the characteristics of fibroblasts," *Nature Scientific Reports*, vol. 6, Article number: 32993 (2016), Zhang et al. "Exosomes derived from human embryonic mesenchymal stem cells promote osteochondral regeneration," *Osteoarthritis and Cartilage*, vol. 24, Issue 12, December 2016, pp. 2135-2140, and Wu et al. "MSC-exosome: A novel cell-free therapy for cutaneous regeneration," *Cytotherapy*, vol. 20, Issue 3, Mar. 2018, pp. 291-301.

Generally, the system hereof involves a bioelectric stimulator controlling release of SDF-1, IGF-1, HGF, EGF, VEGF, PDGF, eNOS, follistatin, Activin A and B, and tropoelastin.

SDF-1 is generally for recruiting stem cells and maturing blood vessels. IGF-1 is for DNA repair. HGF is for tissue regeneration. EGF grows tissue. VEGF grows blood vessels. PDGF is a second stem cell homing factor and helps tissue regeneration. eNOS dilates blood vessels. Follistatin promotes muscle growth. Activin A and B regenerates nerve cells and neurons. Tropoelastin increases elasticity of all tissues especially the skin.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal treatment or regeneration.

An infusion and electrode wide area pitch may be constructed by cutting conduction polymer to shape and forming plastic into a flat bag with outlet ports in strategic locations.

Micro stimulators may be purchased or constructed in the same manner heart pacemakers have been made since the 1960's. Micro infusion pumps can be purchased or produced similar to how they have been produced for drug, insulin, and pain medication delivery since the 1970's. The programming computer can be standard laptop computer. The programming wand customary to wireless programming wands may be used to program heart pacers.

Any one of the protein expression signals work well on their own, but they work better together. SDF-1 is the most powerful regeneration protein followed by IGF-1.

Wireless, single lumen infusion pacing lead or an infusion conduction wide array patch may all be used to deliver the regeneration signals and substances to the area of interest or they may be used in combination.

A re-charging wand for use herein is preferably similar to the pacemaker re-charging wand developed by Alfred Mann in the early 1970's for recharging externally implantable pacemakers.

A preferred composition includes adipose-derived cells (or bone marrow-derived MSCs or any pluripotent stem cell, such as iPS cells) and growth factor mix which should include (SDF-1, IGF-1, EGF, HGF, PDGF, VEGF, eNOS, activin A, activin B, follistatin, and tropoelastin plus selected exosomes (miR-146a, miR-294, mES-Exo) plus selected alkaloids (harmine and tetrahydroharmine) plus selected anti-inflammatory factors plus nutrient hydrogel (IGF-1, SDF-1, HGF plus FGF) plus skin matrix. Also, preferably included are amniotic fluid, placenta, or cord blood when available.

The concentration of cells in the compositions is preferably about 50,000,000 cells/ml. The amniotic fluid is preferably as described in Pierce et al. "Collection and characterization of amniotic fluid from scheduled C-section deliveries," Cell Tissue Bank, DOI 10.1007/s10561-016-9572-7 (Springer, 2012) and is available from Irvine Scientific.

Described is a method of activating a tissue to differentiate a stem cell or to stimulate the tissue to produce a protein. The protein is selected from the group consisting of insulin-like growth factor 1 ("IGF-1"), epidermal growth factor ("EGF"), hepatocyte growth factor ("HGF"), platelet-derived growth factor ("PDGF"), endothelial NOS ("eNOS"), vascular endothelial growth factor ("VEGF"), activin A, activin B, follistatin, interleukin 6 ("IL-6"), hypoxia-inducible factor 1-alpha ("HIF-1-α"), and tropoelastin, the method including: stimulating the, e.g., human tissue with an electrical signal appropriate for the protein and tissue.

In such a method, when the electrical signal includes (within 15%): 0.1V applied at a frequency of about 50 Hz with a duration of about three (3) minutes (wherein the electrical signal is as measured three (3) mm deep into the tissue), the protein produced is VEGF.

In such a method, when the electrical signal includes (within 2%): 200 picoamps for about 10 seconds for about one (1) hour and the pulse has an amplitude of about 5 volts and a width of about 0.5 milliseconds for about 1 hour, with a duration of about one (1) minute (wherein the electrical signal is as measured three (3) mm deep into the tissue), stem cells differentiate.

In such a method, when the electrical signal includes (within 15%): 10V at 50 HZ and 100 HZ for about 12 hours each (duration 1 minute) (wherein the electrical signal is as measured three (3) mm deep into the tissue), the protein produced is follistatin.

In such a method, when the electrical signal includes (within 15%): 3.5V stimulation in 10 second bursts, 1 burst every 30 seconds at a frequency of about 50 HZ (duration 5 minutes) (wherein the electrical signal is as measured three (3) mm deep into the tissue), the protein produced is HGF.

In such a method, when the electrical signal includes (within 15%): 3mv with a frequency of about 22 Hz, and a current of about 1 mA for about fifteen (15) minutes and 3ma for about fifteen (15) minutes (duration 5 minutes) (wherein the electrical signal is as measured three (3) mm deep into the tissue), the protein produced is IGF-1.

In such a method, when the electrical signal includes (within 15%): 0.06 V with 50Z alternating electrical field and a current of about 1ma for about fifteen (15) minutes and 3ma for about fifteen (15) minutes (duration 2 minutes) (wherein the electrical signal is as measured three (3) mm deep into the tissue), the protein produced is tropoelastin.

In such a method, when the electrical signal includes (within 15%): alternating high-frequency (HF) and medium-frequency signals (MF), symmetric, biphasic, trapezoid pulses, with 400-µs pulse duration and 1.5/1-s ramp-up/ramp-down duration, respectively (wherein the electrical signal is as measured three (3) mm deep into the tissue), the protein produced is eNOS. In such a method, when the HF consists of about 75 Hz pulses with six (6) seconds on and 21 seconds off for about fifteen (15) minutes. In such a method, when the MF consists of about 45 Hz pulses with 5 seconds on 12 seconds off for about fifteen (15) minutes followed by stimulation duration set as 20 minutes. In such a method, when the electrical signal includes (within 15%): 1 Hz stimulation, stimulation applied for about nine (9) seconds, followed by a one (1) second silent period, a total of about 1080 stimulations for about 20 minutes. In such a method, when the electrical signal includes (within 15%): 20 Hz stimulation, stimulation applied for about two (2) seconds, followed by silent period for about 28 seconds, a total of about 1600 stimulations for about 20 minutes (duration 2 minutes).

In such a method, when the electrical signal includes (within 15%): 6mv at 150 HZ Monophasic square wave pulse 0.1 ms in duration current of fifteen (15) mA for about fifteen (15) minutes (duration two (2) minutes) (wherein the electrical signal is as measured three (3) mm deep into the tissue), the protein produced is Activin B.

In such a method, when the electrical signal includes (within 15%): 10 V/cm, pulse-width 180 µs, 500 Hz (duration nine (9) minutes) (wherein the electrical signal is as measured three (3) mm deep into the tissue), the protein produced is EGF.

For example, upregulation of IGF-1, VEGF, and SDF-1 was achieved in cardiomyocytes using such signals. Upregulation of SDF-1 was achieved in pig heart. Upregulation of VEGF, endothelial NOS ("eNOS"), hypoxia-inducible factor 1-alpha ("HIF-1-a"), and IL-6 was achieved in eye cells.

Also described is a method of activating a tissue to produce stromal cell-derived factor 1 ("SDF-1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 µs, wherein the electrical signal is as measured three (3) mm deep into the tissue (e.g., preferably for a period of time of about 20 minutes).

Further described is a method of activating a tissue to attract a stem cell, the method including: stimulating the (e.g., human) tissue with an electrical signal, wherein the electrical signal includes (within 2%): fifteen (15) mV and a current of about 500 picoamps at 70 pulses per minute for about three (3) hours and 20 pulses per minute, a pulse amplitude of from about 2.5-6 volts, and a pulse width of from about 0.2-0.7 milliseconds for about three (3) hours for about three (3) minutes, wherein the electrical signal is as measured three (3) mm deep into the tissue.

In some cases, SDF-1 recruits via a presumed homing signal new reparative stem cells to the damaged skin. VEGF causes new nutrient and oxygen producing blood vessels to grow into the area being treated. IGF-1 repairs damaged cells and tissues. Follistatin repairs damaged muscle. Tropoelastin adds elasticity to treated tissues making them more compliant. HGF aides in all repair processes. All of these proteins work together to fully regenerate/rejuvenate the skin tissue over time.

The healing process can be accelerated with the use of a micro infusion pump that is filled with various types of stem cells and growth factors and in some cases drugs.

What follows are preferred signals from the stimulator. For example, described are two PDGF expression control signals, one low voltage and one higher voltage. The test tissue is sheep heart tissue. The test cells are mesenchymal stem cells.

30% PDGF increase: 3 V/cm, 10 Hz, 2 micro amps (0.000002 amps) and the pulse duration 0.2 ms.

230% PDGF increase: 20 V/cm 100 Hz, 0.25 mA (2.5e-7 amps) and pulse duration of 40 pulses/s, width of 100 µs.

40 minute treatment cycles 2 times a week for 4 weeks and then 3 times a week for 12 weeks.

PDGF Signal: 20V for 1 minute, 20 mV for 10 minutes, current of 0.25 mA, pulse duration of 40 pulses/s, pulse width of 100 µs, and frequency of 100 Hz for 5 minutes followed by 528 Hz for 3 minutes and 432 Hz for 3 minutes and 50 Hz for 3 minutes.

VEGF—Blood vessel sprouting growth: 0.1V applied at a frequency of 50 Hz. Duration 3 minutes. In certain embodiments, the duration can be for a time of, e.g., from 10 to 40 minutes, wherein the percentage VEGF expression increases with time.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 μs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Stem cell differentiation signals to become muscle: 200 picoamps for 10 seconds for 1 hour and the pulse has an amplitude of 5 volts and a width of 0.5 milliseconds for 1 hour. Duration 1 minute. Another method is to reverse polarity and drop the voltage.

Stem cell differentiation signal to become skin: low-voltage square wave with 60 ms pulse duration for one to seven cycles, then reverse polarity to a negative square wave for one to fourteen cycles, which repeats, delivering 200 microAmps.

Follistatin—(muscle growth) production signal: 10V at 50 HZ and 100 HZ 0.25 mA. Duration 1 minute.

HGF—Hepatocyte growth factor (arrhythmia reduction) signal: 3.5V stimulation in 10 second bursts, 1 burst every 30 seconds at frequency 50 HZ. Duration 5 minutes.

IGF-1: 3mv with electric frequency of 22 Hz, and electric current of 1 mA for 15 minutes and 3ma for 15 minutes. Duration 5 minutes.

Tropoelastin: 0.06 V with 50Z alternating electrical field and electric current of 1ma for 15 minutes and 3ma for 15 minutes. Duration 2 minutes.

eNOS: Alternating high-frequency (HF) and medium-frequency signals (MF): Symmetric, biphasic, trapezoid pulses, with 400-μs pulse duration and 1.5/1-s ramp-up/ramp-down duration, respectively. HF consisted of 75 Hz pulses with 6 second on-21 second off for 15 minutes. MF consisted of 45 Hz pulses with 5 second on-12 second off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

Activin B: 6mv at 150 HZ Monophasic square wave pulse 0.1 ms in duration current of 15 mA for 15 minutes. Duration 2 minutes.

EGF—10 V/cm, pulse-width 180 μs, 500 Hz. Duration 9 minutes.

FIGS. 4-14 are images of the corresponding signals with the name, voltage, and frequency of each signal written on each image. eNOS and differentiation signals were omitted due to of complexity or lack of frequency parameters. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Figure 4:
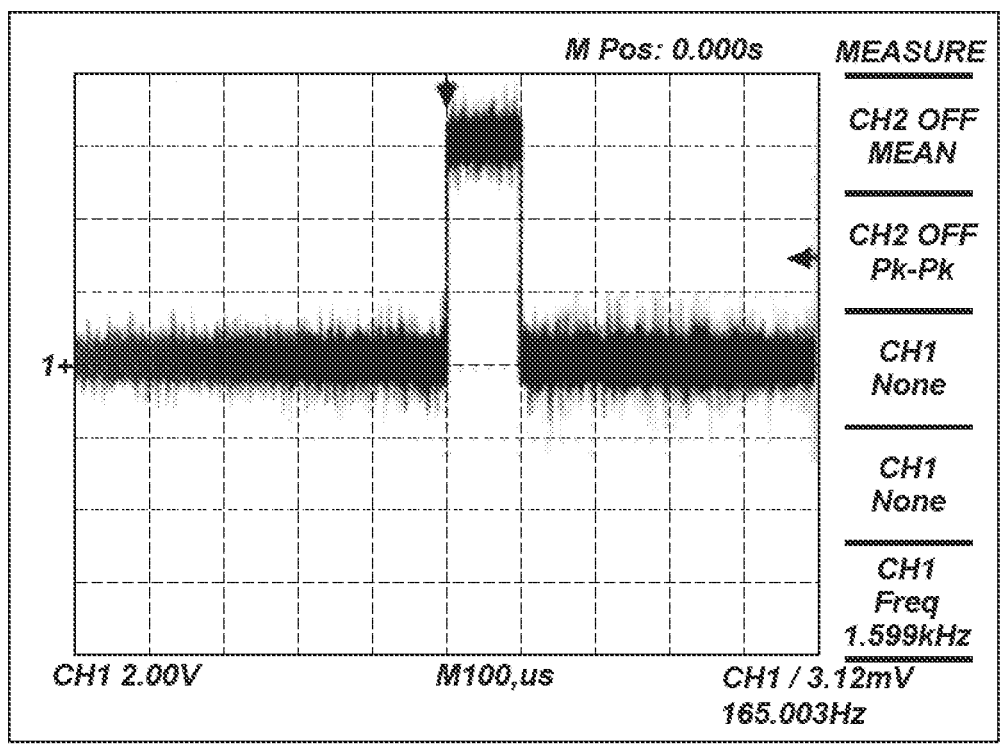
FIG. 4 depicts an image of the signal (voltage and frequency) associated with producing and/or expressing Activin B at 6.0 mV, pulse width 100 μs, square wave.
Figure 5:
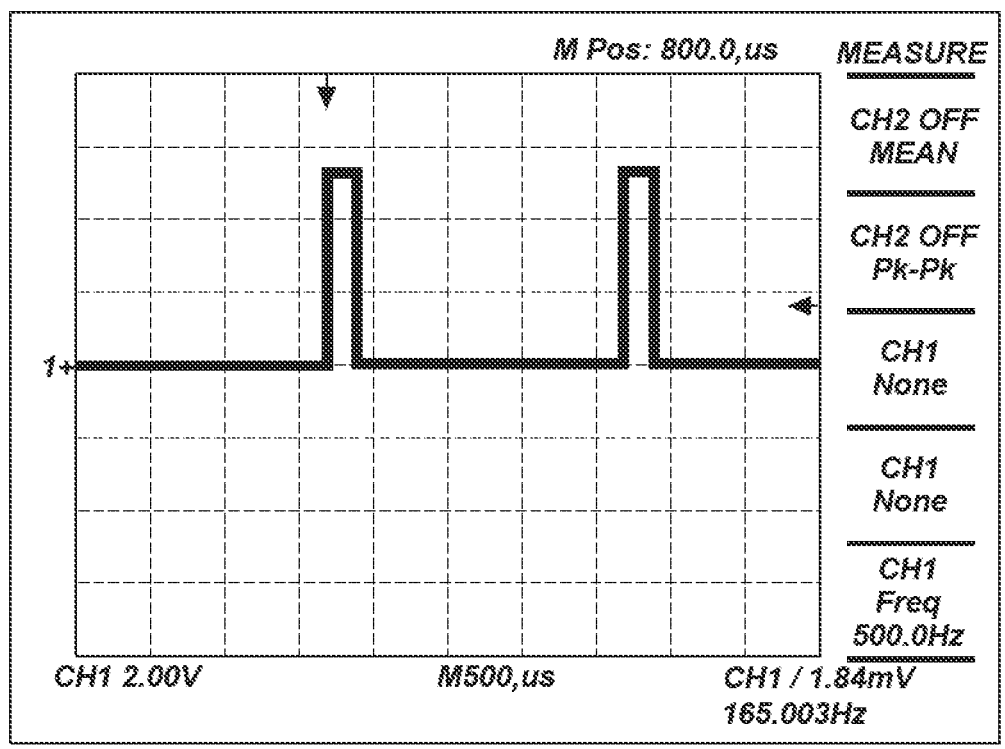
FIG. 5 depicts an image of the signal (voltage and frequency) associated with producing and/or expressing EGF at 10V/cm (5V here), 500 Hz, pulse width 180 μs, square wave.
Figure 6:
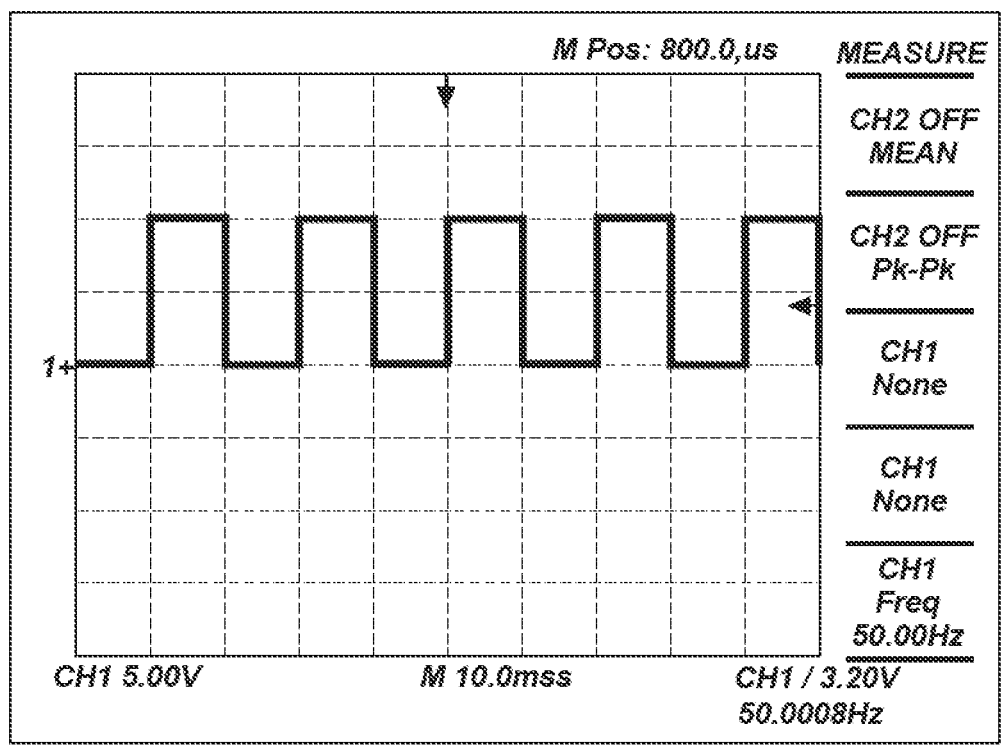
FIG. 6 depicts an image of the signal (voltage and frequency) associated with producing and/or expressing follistatin at 10V/cm, 50 Hz, square wave.
Figure 7:
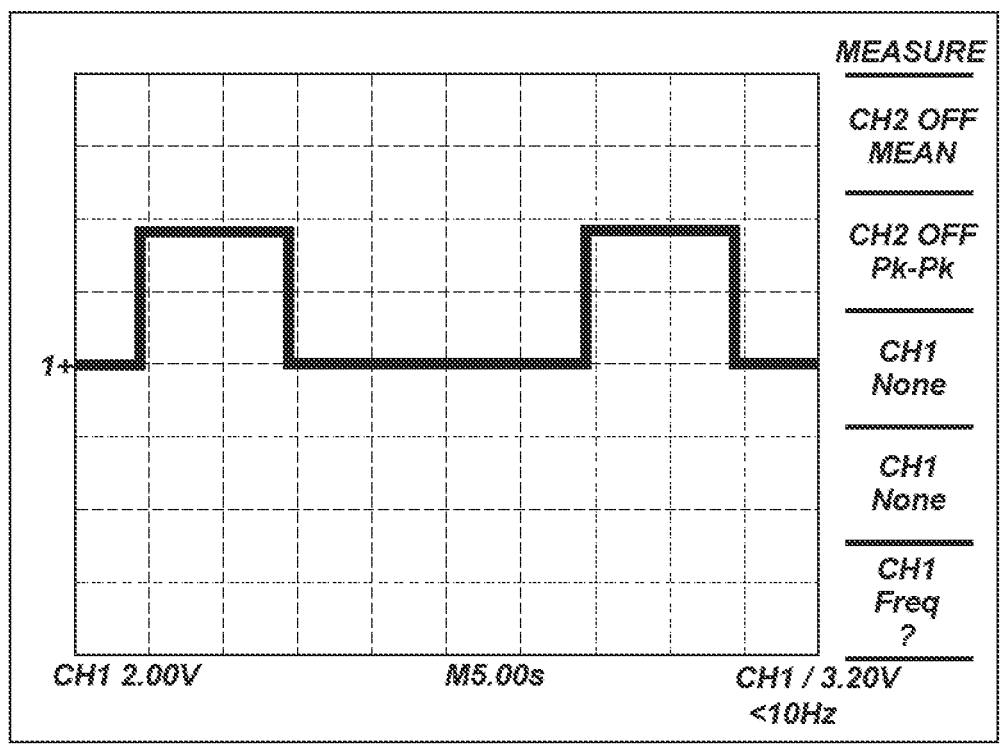
FIG. 7 depicts an image of the signal (voltage and frequency) associated with producing and/or expressing HGF at 3.5V, 10 second burst every 30 seconds, square wave.
Figure 8:
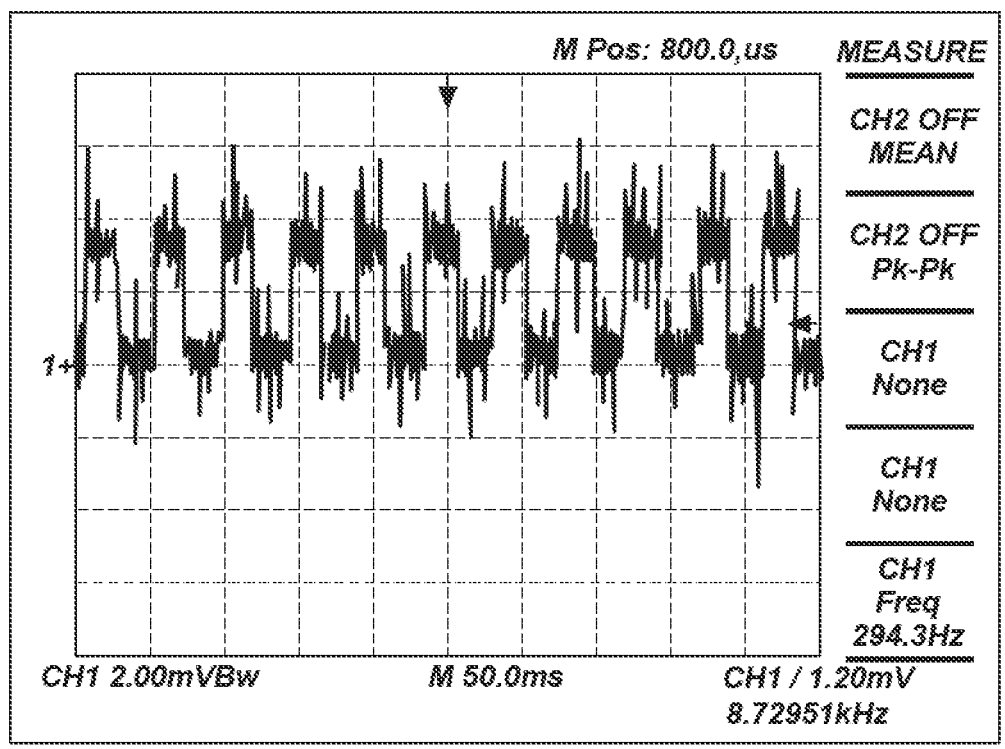
FIG. 8 depicts an image of the signal (voltage and frequency) associated with producing and/or expressing IGF-1: 3.0 mV, 22 Hz, square wave.
Figure 9:
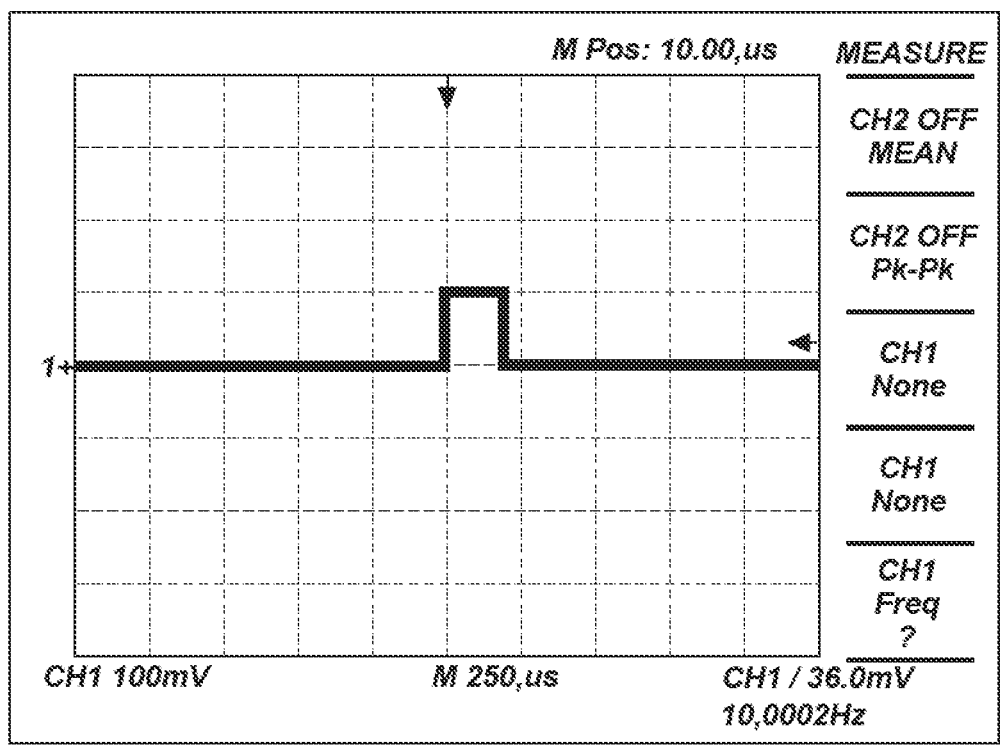
FIG. 9 depicts an image of the signal (voltage and frequency) associated with producing and/or expressing PDGF30%: 3V/cm (100 mV here), 10 Hz, pulse width 200 μs, square wave.
Figure 10:
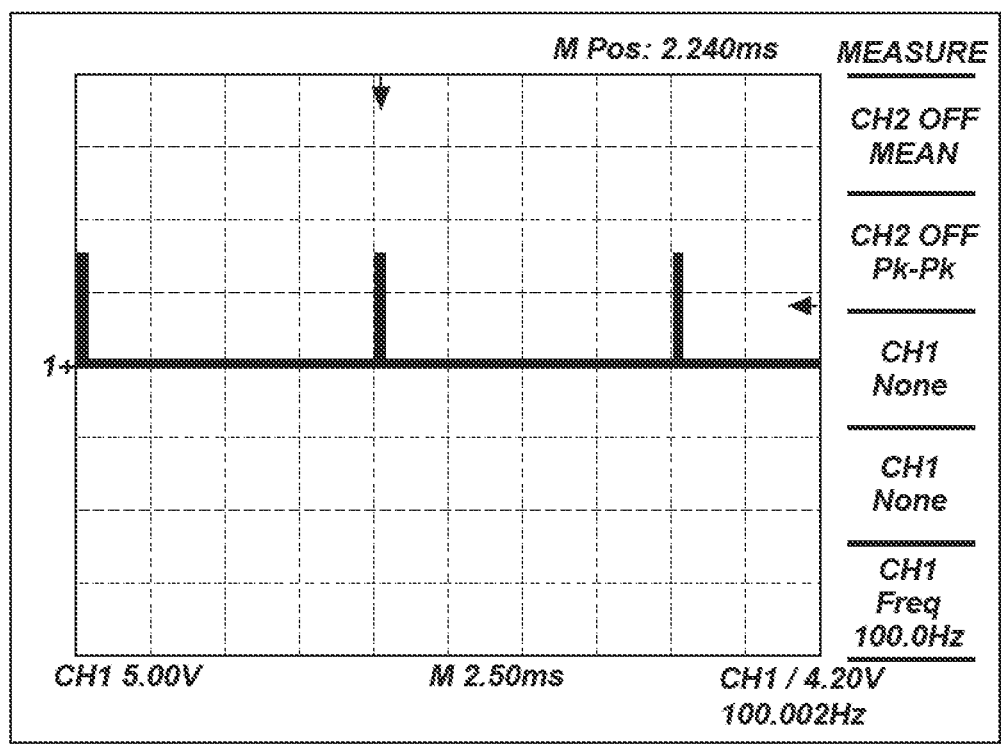
FIG. 10 depicts an image of the signal (voltage and frequency) associated with producing and/or expressing PDGF230%: 20V/cm (7.0V here), 100 Hz, pulse width 100 μs, square wave.
Figure 11:
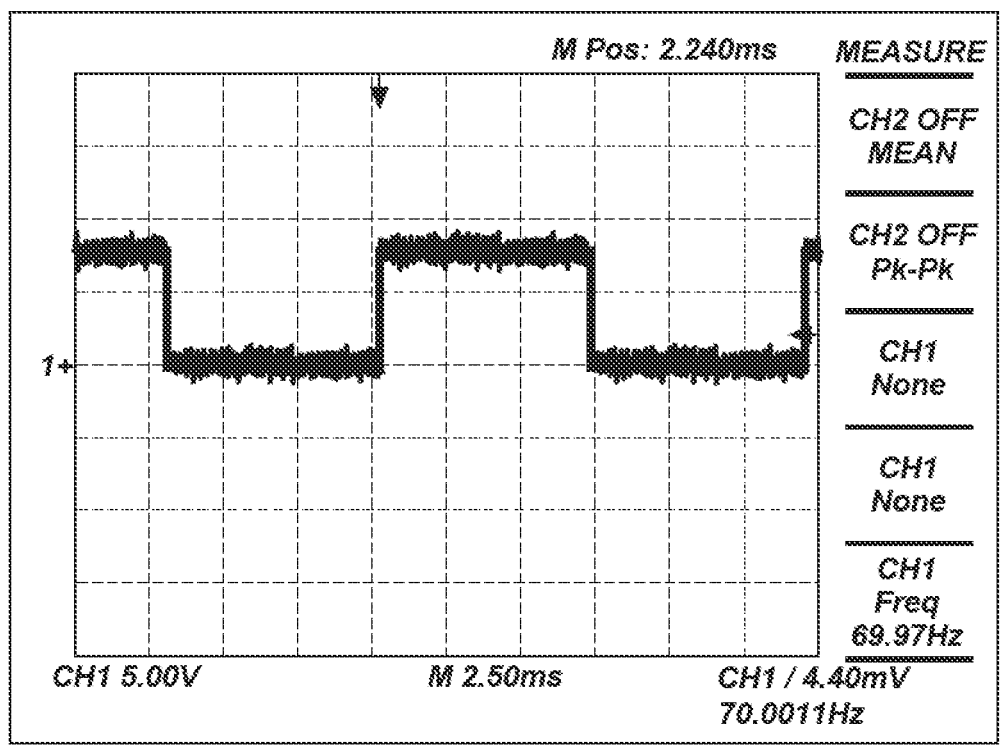
FIG. 11 depicts an image of the signal (voltage and frequency) associated with stem cell proliferation: 15 mV, 70 Hz, square wave.
Figure 12:
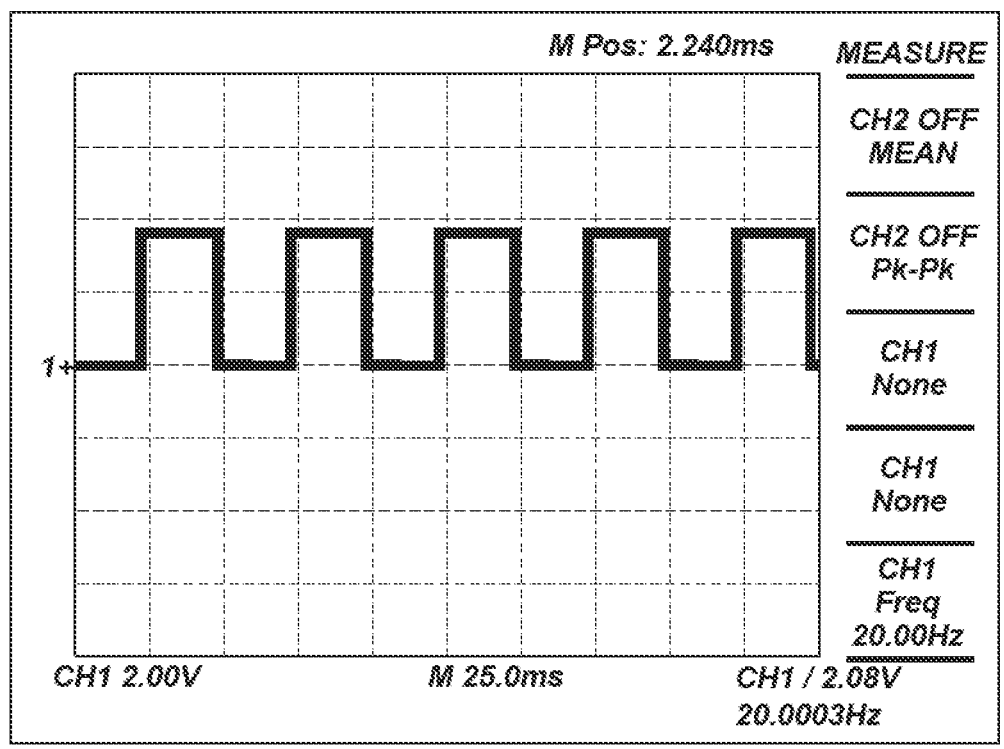
FIG. 12 depicts an image of the signal (voltage and frequency) associated with stem cell proliferation: 2.5-6.0 V (4V here), 20 Hz, pulse width 200-700 μs, square wave.
Figure 13:
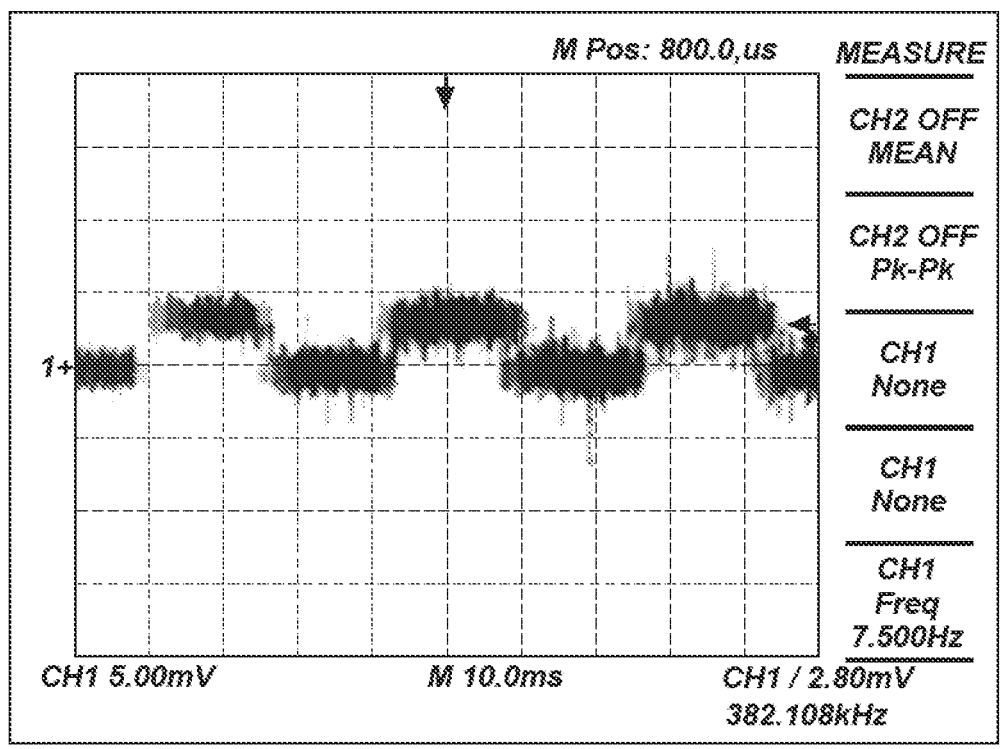
FIG. 13 depicts an image of the signal (voltage and frequency) associated with producing and/or expressing SDF-1: 3.5 mV, 30 Hz, square wave.
Figure 14:
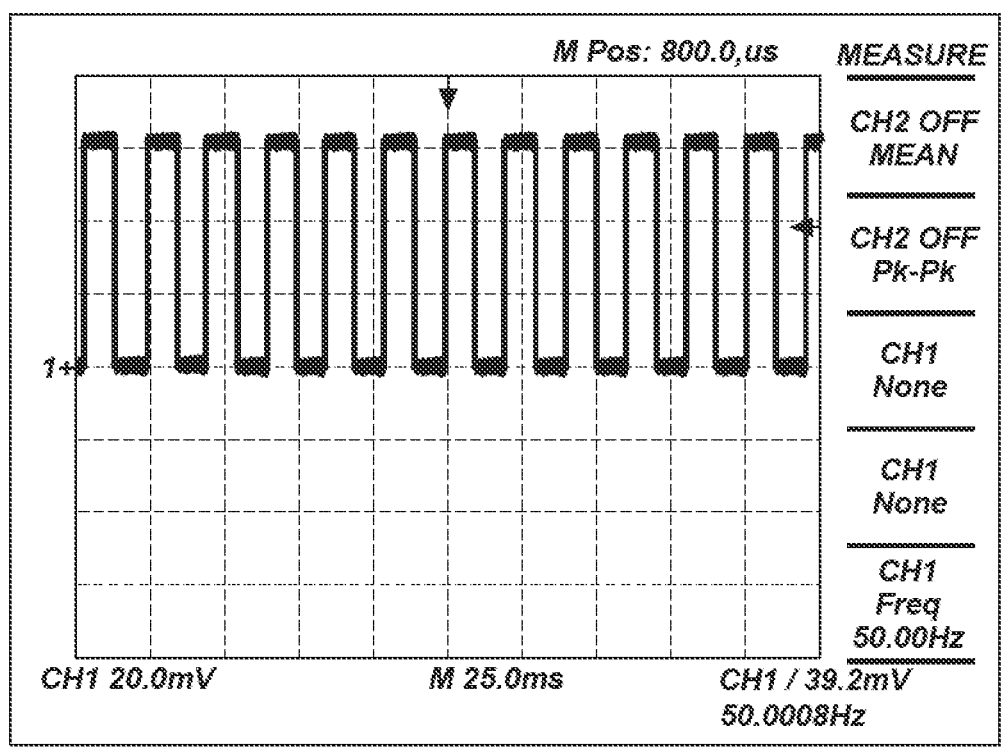
FIG. 14 depicts an image of the signal (voltage and frequency) associated with producing and/or expressing tropoelastin: 60 mV, 50 Hz, square wave.
Figure 15:
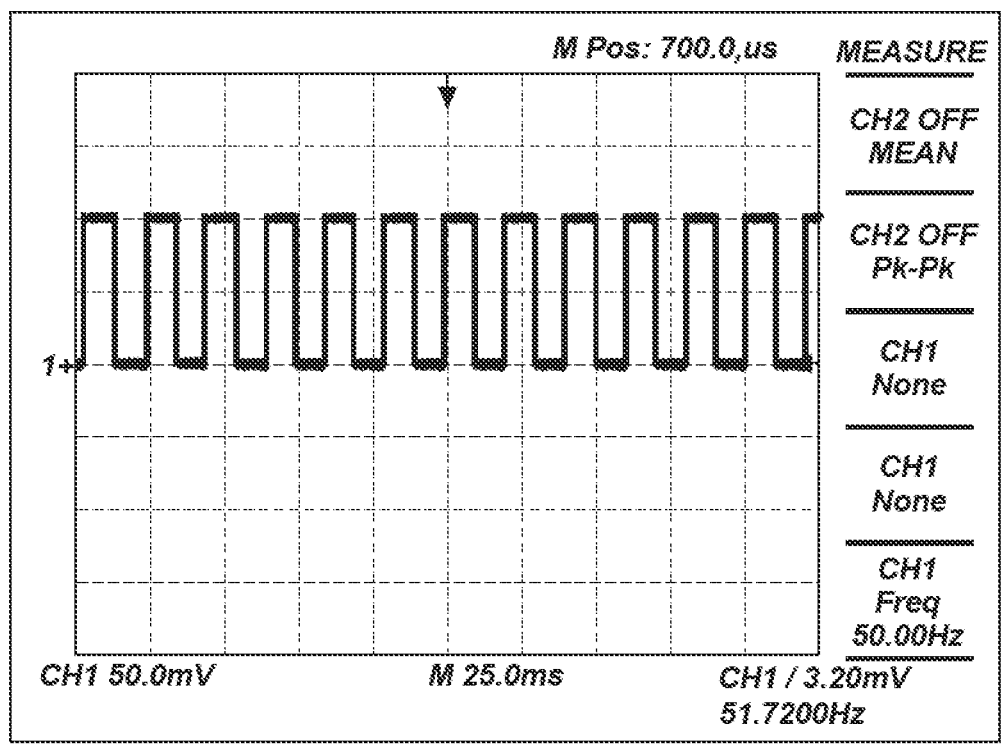
FIG. 15 depicts an image of the signal (voltage and frequency) associated with producing and/or expressing VEGF: 100 mV, 50 Hz, square wave.
Figure 16:
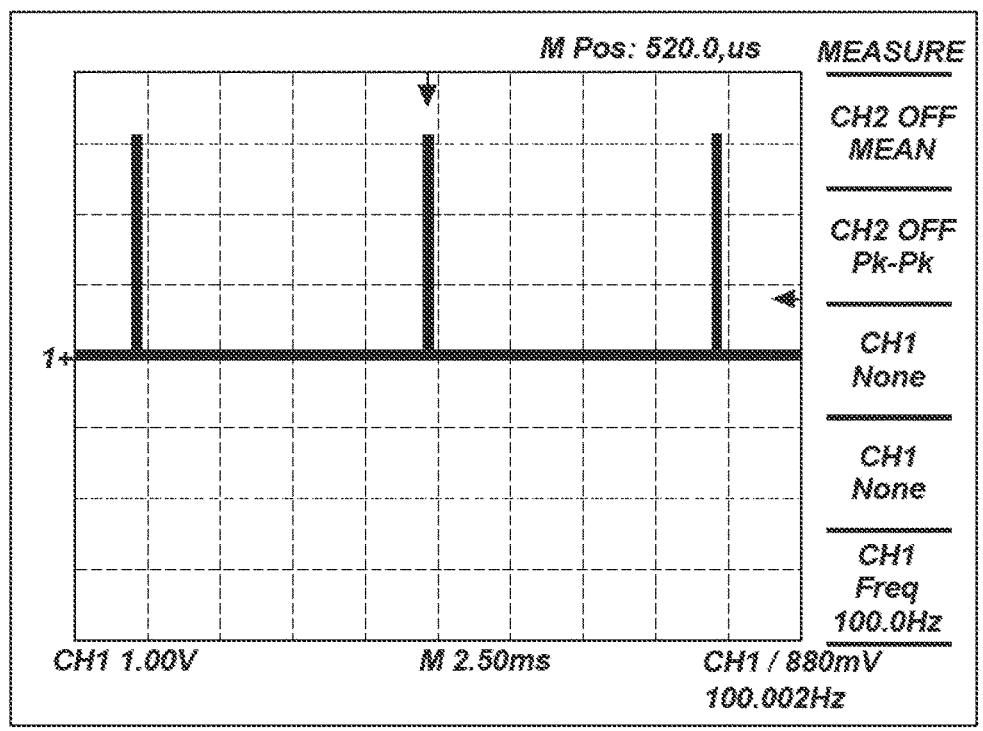
FIG. 16 depicts an image of the signal (voltage and frequency) associated with producing and/or expressing SDF-1 ($2^{nd}$ part): 0.25 mA (3.0V shown here), 100 Hz, 100 μs pulse width, square wave.

Specifically, FIG. 4 depicts an image of the signal (voltage and frequency) associated with producing and/or expressing Activin B at 6.0 mV, pulse width 100 μs, square wave on a TEKTRONIX® TPS 2024 four channel digital storage oscilloscope. FIG. 5 depicts an image of the signal (voltage and frequency) associated with producing and/or expressing EGF at 10V/cm (5V here), 500 Hz, pulse width 180 μs, square wave. FIG. 6 depicts an image of the signal (voltage and frequency) associated with producing and/or expressing follistatin at 10V/cm, 50 Hz, square wave. FIG. 7 depicts an image of the signal (voltage and frequency) associated with producing and/or expressing HGF at 3.5V, 10 second burst every 30 seconds, square wave. FIG. 8 depicts an image of the signal (voltage and frequency) associated with producing and/or expressing IGF-1: 3.0 mV, 22 Hz, square wave (for a time of, e.g., from 10 to 40 minutes). FIG. 9 depicts an image of the signal (voltage and frequency) associated with producing and/or expressing PDGF30%: 3V/cm (100 mV here), 10 Hz, pulse width 200 μs, square wave. FIG. 10 depicts an image of the signal (voltage and frequency) associated with producing and/or expressing PDGF230%: 20V/cm (7.0V here), 100 Hz, pulse width 100 μs, square wave. FIG. 11 depicts an image of the signal (voltage and frequency) associated with stem cell proliferation: 15 mV, 70 Hz, square wave. FIG. 12 depicts an image of the signal (voltage and frequency) associated with stem cell proliferation: 2.5-6.0 V (4V here), 20 Hz, pulse width 200-700 μs, square wave. FIG. 13 depicts an image of the signal (voltage and frequency) associated with producing and/or expressing SDF-1: 3.5 mV, 30 Hz, square wave. FIG. 14 depicts an image of the signal (voltage and frequency) associated with producing and/or expressing tropoelastin: 60 mV, 50 Hz, square wave. FIG. 15 depicts an image of the signal (voltage and frequency) associated with producing and/or expressing VEGF: 100 mV, 50 Hz, square wave. FIG. 16 depicts an image of the signal (voltage and frequency) associated with producing and/or expressing SDF-1 ($2^{nd}$ part): 0.25 mA (3.0V shown here), 100 Hz, 100 μs pulse width, square wave.

In certain embodiments, a subject's skin is first scanned or analyzed with a device to determine what his or her needs may be before treatment begins. The scanning/analysis can be by, e.g., generating mechanical vibrations at position adjacent the location to be an analyzed as described in, e.g., US 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a *Xenopus* model," Dis. Models & Mech. 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents" J. Ren. Nutr., 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of skin, sometimes by placement of a bion coil reader and transmitter in the skin, and direct that information to a computer. The computer stores the bioelectrical read measurements of diseased skin and healthy skin and makes a comparative exam classifying the skin into one category or another, which is much like a doctor using information to make a diagnosis.

Scanners such as the Ina'Chi scanner, the Quantum Magnetic Resonance Analyzer (QMRA), the 3D Quantum Health Analyzer Scan whole body organ health 2, BODY-SCAN® scanner, and the "BIONic muscle spindle" are also useful.

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's tissue(s) are collected by appropriately positioning the sensor with respect to the portion of the subject's tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

In certain embodiments, bioelectric signaling is applied to the area of skin to be treated in approximate 28 minute treatment sessions twice a week for, e.g., up to 16 weeks (32 times total) utilizing, e.g., a benchtop bioelectric stimulator and face mask. The bioelectric signaling is preferably applied to the skin area to be treated as follows: (a) SDF-1 homing signal to recruit stem cells to skin for about seven (7) minutes, (b) IGF-1 DNA repair signal for about four (4) minutes, (c) tropoelastin signal to increase skin elasticity for about twelve (12) minutes, and (d) blood circulation improvement signal sequence VEGF for about five (5) minutes.

This "basic" program can be supplemented by supplying further signaling (i.e., in addition to the foregoing) by applying the following bioelectric signaling: (e) PDGF, HIF1a, eNOS, CXCL5 for advanced blood circulation, (f) Stem cell proliferation, (g) Stem cell differentiation control, (h) extended PRF protein release, (i) HGF for skin regeneration, and (j) EGF for skin regeneration.

A preferred treatment protocol for facial skin regeneration, rejuvenation, and/or treatment comprises: 30 minutes of bioelectric treatments (e.g., in clinic), twice a week for 16 weeks; PRF, amniotic fluid, stem cell injections (via, e.g., DERMAPEN™) once a week every four weeks for 16 weeks (four times total); amniotic fluid membrane application once a week every eight weeks for 16 weeks (two times total); daily bioelectric treatment (e.g., at home) for at least 15 minutes a day for 16 weeks; bioelectric micro-current conductive globe facial massage once a week every four weeks for 16 weeks (four times total); electroacupuncture once a week every eight weeks for 16 weeks (two times total); and LUMANAIRE™ hydrogel skin cream applied morning and night every day for 16 weeks.

A preferred protocol follows. First, bioelectric signaling is applied to the area to be treated in approximate 40 minute treatment sessions twice a week for up to 16 weeks (32 times total) utilizing, e.g., a benchtop bioelectric stimulator and face mask. The preferably in-clinic precision bioelectric signaling applied to the area is as follows:

(first) SDF-1 homing signal to recruit stem cells to skin for about seven (7) minutes, (second) stem cell to skin differentiation signal for about three (3) minutes, (third) IGF-1 DNA repair signal for about four (4) minutes, (fourth) EGF epidermal growth factor signal skin repair for about three (3) minutes, (fifth) Tropoelastin signal to increase skin elasticity for about twelve (12) minutes, (sixth) Blood circulation improvement signal sequences VEGF, PDGF, eNOS, HIF1a, CXCL5, EGF, HGF, and SDF-1 for about five (5) minutes, (seventh) Muscle-toning signal follistatin for about two (2) minutes, (eighth) SDF-1 again for about one (1) minute, and (ninth) Stem cell to skin differentiation again for about one (1) minute.

Then, the foregoing bioelectric signaling is preferably combined with any or all of the following:

DERMAPEN™ Micro Needle array delivery of a skin regeneration composition mix that includes adipose tissue derived stem cells, exosomes, micro RNAs, selected alkaloids, hydrogel skin matrix, elastin, oxygenated nanoparticles, platelet rich fibrin ("PRF"), amniotic fluid, and selected growth factors such as SDF-1, IGF-1, EGF, HGF, and PDGF or any combination thereof once a month for about four (4) months (four times total)

DERMAPEN™ micro needle array delivery of PRF once a month for about four (4) months (four times total). May or may not be bioelectric energy enhanced.

DERMAPEN™ micro needle array delivery of amniotic fluid once a month for about four (4) months (four times total)

DERMAPEN™ micro needle array delivery of adipose tissue derived stem cells once every two months for about four (4) months (two times total)

At home Prizm Medical electrical stimulation with conductive electro-massaging gloves once a week for 15 minutes for 16 weeks (sixteen times total)

Electroacupuncture with, e.g., simple electroacupuncture pen once a month for about four (4) months (four times total)

LED pulsed light therapy 10 minutes twice a week via combination bioelectric and light mask (32 times total)

Amniotic fluid membrane dressings once a month left on for one hour (four times total).

DERMAPEN™ micro needle array delivery of oxygenated nanoparticles once a month for four months (four times total)

DERMAPEN™ micro needle array delivery of hydrogel skin matrix once every other month for four months (two times total)

Application of a hydrogel and stem cell matrix-based skin cream twice a day for about sixteen (16) weeks once in the morning and once before bed (224 times total). May or may not be light or bioelectric energy activated or enhanced.

Used in conjunction with GOSEAR™ electroacupuncture pen, DERMAPEN™ microneedle array for delivering stem cells, amniotic fluid, PRF. PRF bedside processing device plus bioelectric PRF equals "BPRF."

The invention is further described with the aid of the following illustrative Examples.

Examples

The study is to enroll and treat patients to assess improvement in the appearance of facial wrinkles utilizing a bioelectric or biologics (PRF and amniotic fluid) therapy or a combination of bioelectric and biologics therapy. The study is to enroll and treat a minimum of 49 subjects (23 in treatment Group A receiving a bioelectric treatment alone, 23 in treatment Group B receiving biologics treatment alone and 23 in Group C receiving combined bioelectric and biologics treatment) with moderate facial wrinkles corresponding to a grade of 4-6 on the validated Fitzpatrick Wrinkle Assessment Scale.

Group A=Active Comparator: Bioelectric Treatment Alone (treatment of facial wrinkle(s) with bioelectric treatment only and hydrogel skin cream). Devices: SkinStim Bioelectric Stimulation twice a week for 30 minutes for 12 weeks and once a week 20 minutes electro face massages with Prizm Medical stimulator and conductive gloves and hydrogel skin cream applied twice a day morning and evening.

Group B=Active Comparator: Biologics Treatment Alone (treatment of facial wrinkle with PRF and amniotic fluid both delivered via a DERMAPEN™ micro needle array and hydrogel skin cream comparison of bioelectric versus biologics versus combined bioelectric and biologics therapies).

Group C: Active Comparator: Combined Bioelectric and Biologics Treatment (treatment of facial wrinkle with bioelectric and biologic treatments) Devices: SkinStim Stimulation twice a week for 30 minutes for 12 weeks and once a week 20 minute electro face massages with Prizm Medical stimulator and conductive gloves and Biologics: Autologous PRF and amniotic fluid applied via DERMAPEN™ microneedle array delivery once a month for 3 months and hydrogel skin cream applied twice a day morning and evening comparison of bioelectric versus biologics versus combined bioelectric and biologics therapies Primary Outcome Measure:

1. Fitzpatrick Wrinkle Assessment [Time Frame: change in Fitzpatrick Wrinkle Score between baseline and 90 days post treatment assessment.]

Subject photos will be evaluated using the 9-point Fitzpatrick Wrinkle Assessment Scale at all follow up visits. An improvement is noted by a decrease in the numeric Fitzpatrick Wrinkle score. The Fitzpatrick Wrinkle Assessment ranges from 1-9. Wrinkle Score between baseline and 90 days post treatment assessment. Positive values indicate an increase in score, while negative values indicate a decrease.

REFERENCES (The contents of the entirety of each of which is incorporated herein by this reference.)

Prochazka et al. "Cocktail of Factors from Fat-derived Stem Cells Shows Promise for Critical Limb Ischemia" http://www.sciencenewsline.com/news/2016012204520017.html (Jan. 21, 2016).

Salcedo et al. "Low current electrical stimulation upregulates cytokine expression in the anal sphincter," *Int. J. Colorectal Dis.*, 2012 February; 27(2):221-5. doi: 10.1007/s00384-011-1324-3. Epub (October 2011).

"What Is Elastin?" keracyte.com/index.php/site/page?view=whatIsElastin

Park et al. "Effects of SM-215 on Hair Growth by Hair Follicle Stimulation," *Indian Journal of Science and Technology*, Vol 8(25), DOI: 10.17485/ijst/2015/v8i25/80263, (October 2015).

Thattaliyath et al. "Modified Skeletal Myoblast Therapy For Cardiac Failure Using AAV SDF-1," *Proc. Intl. Soc. Mag. Reson. Med.* 16, p. 579 (2008).

"Electrical brain stimulation could support stroke recovery," sciencedaily.com/releases/2016/03/160316151108.htm (Mar. 16, 2016).

"Electric Tumor Treatment Fields," No. 0827 Policy, aetna.com/cpb/medical/data/800_899/0827.html (Nov. 18, 2016).

D. Grady "Electrical Scalp Device Can Slow Progression of Deadly Brain Tumors," *New York Times*, https://www.nytimes.com/2014/11/16/health/electrical-scalp-device-can-slow-progression-of-deadly-brain-tumors.html?_r=0 (Nov. 15, 2014).

B. Borgobello "FDA approves the treatment of brain tumors with electrical fields," *New Atlas*, http://newatlas.com/treatment-of-brain-tumors-with-electrical-fields/21433/ (Feb. 13, 2012).

Hopkins Medicine "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_defibrillators_icds_85,P00234/.

Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf "FDA Approves Algovita Spinal Cord Stimulation System from Greatbatch," http://www.odtmag.com/contents/view_breaking-news/2015-12-02/fda-approves-algovita-spinal-cord-stimulation-system-from-greatbatch (Dec. 2, 2015).

Mass Device "Greatbatch wins FDA PMA for Algovita SCS," http://www.massdevice.com/greatbatch-wins-fda-pma-for-algovita-scs/ (Dec. 1, 2015).

Sahoo and Losordo "Exosomes and Cardiac Repair After Myocardial Infarction," *Circulation Research*, 114:333-344 (Jan. 16, 2014).

Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (March 2008).

W. Hoffmann "Regeneration of the gastric mucosa and its glands from stem cells," *Curr. Med. Chem*, 15(29):3133-44 (2008).

Cerrada et al. "Hypoxia-Inducible Factor 1 Alpha Contributes to Cardiac Healing in Mesenchymal Stem Cells-Mediated Cardiac Repair," *Stem Cells and Development*, 22(3): 501-511 (2013).

Fatemi et al. "Imaging elastic properties of biological tissues by low-frequency harmonic vibration" Proceedings of the IEEE, 91(10):1503-1519 (October 2003) DOI: 10.1109/JPROC.2003.817865.

Mosteiro et al. "Tissue damage and senescence provide critical signals for cellular reprogramming in vivo." Science, 2016; 354 (6315): aaf4445 DOI: 10.1126/science.aaf4445

Tajima et al. "HIF-1alpha is necessary to support gluconeogenesis during liver regeneration" *Biochem Biophys Res Commun.* 2009 Oct. 2; 387(4):789-94. doi: 10.1016/j.bbrc.2009.07.115. Epub 2009 Jul. 28.

Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (2008).

What is claimed is:

1. A method of treating an area of a subject's skin, the method comprising: applying each of the following exogenous bioelectric signals to the area to be treated as follows:
   for about seven (7) minutes, an exogenous bioelectric signal that recruits stem cells to the area treated,
   for about four (4) minutes, an exogenous bioelectric signal of 3*mv* with electric frequency of 22 Hz, square wave,
   for about twelve (12) minutes, an exogenous bioelectric signal of 60 mV, 50 Hz, square wave, and for about five (5) minutes, an exogenous bioelectric signal that improves blood circulation in the area treated.

2. The method according to claim 1, further comprising: applying exogenous bioelectric signals to the area to be treated as follows:
an exogenous bioelectric signal that causes proliferation of stem cells.

3. The method according to claim 1, further comprising: applying exogenous bioelectric signals to the area to be treated as follows:
for about three (3) minutes, an exogenous bioelectric signal that differentiates stem cells into skin cells.

4. The method according to claim 1, further comprising: applying exogenous bioelectric signals to the area to be treated as follows:
for about three (3) minutes, an exogenous bioelectric signal of 10V/cm, 500 Hz, pulse width 180 μs, square wave.

5. A method of treating an area of a subject's skin, the method comprising: applying each of the following exogenous bioelectric signals to the area to be treated as follows:
a first exogenous bioelectric signal to recruit stem cells to the skin for about seven (7) minutes,
a second exogenous bioelectric signal to differentiate the stem cells into skin cells for about three (3) minutes,
a third exogenous bioelectric signal of 3 mV with electric frequency of 22 Hz, square wave for about four (4) minutes,
a fourth exogenous bioelectric signal of 10V/cm, 500 Hz, pulse width 180 ps, square wave for about three (3) minutes,
a fifth exogenous bioelectric signal of 60 mV, 50 Hz, square wave for about twelve (12) minutes,
a sixth exogenous bioelectric signal to improve blood circulation in the area for about five (5) minutes,
a seventh exogenous bioelectric signal of IOV/cm, 50 Hz, square wave for about two (2) minutes,
an eighth exogenous bioelectric signal selected from the group consisting of (a) 30 pulses per second with a voltage of 3.5 mV, and successively alternating currents of 700 to 1500 picoamps, and again with 700 to 1500 picoamps and stimulated with current of 0.25 mA, pulse duration of 40 pulses/s, pulse width of 100 ps, and frequency of 100 Hz, (b) 3.5 mV, 30 Hz, square wave, (c) 0.25 mA, 3.0V, 100 Hz, 100 ps pulse width, square wave, (d) a sequential combination of any thereof for about one (1) minute, and
a ninth exogenous bioelectric signal to differentiate the stem cells in the area into skin cells for about one (1) minute.

6. The method according to claim 5, wherein the first exogenous bioelectric signal comprises an exogenous bioelectric signal selected from the group consisting of
(a) 100 mV, 10 Hz, pulse width 200 μs, square wave,
(b) 3 V/cm, 10 Hz, 2 microAmps and a pulse duration of 0.2 ms,
(c) 20 V/cm 100 Hz, 0.25 mA (2.5e-7 amps) and pulse duration of 40 pulses/s, width of 100 μs,
(d) first 20V, then 20 mV, current of 0.25 mA, pulse duration of 40 pulses/s, pulse width of 100 μs, and frequency of 100 Hz followed by 528 Hz and 432 Hz and 50 Hz,
(e) 30 pulses per second with a voltage of 3.5 mV, and successively alternating currents of 700 to 1500 picoamps, and again with 700 to 1500 picoamps and stimulated with current of 0.25 mA, pulse duration of 40 pulses/s, pulse width of 100 μs, and frequency of 100 Hz,
(f) 20V/cm, 100 Hz, pulse width 100 μs, square wave,
(g) 3.5 mV, 30 Hz, square wave,
(h) 0.25 mA, 3.0V, 100 Hz, 100 μs pulse width, square wave, and
(i) a sequential combination of any thereof.

7. The method according to claim 6, wherein the first exogenous bioelectric signal is selected from the group consisting of
30 pulses per second with a voltage of 3.5 mV, and successively alternating currents of 700 to 1500 picoamps, and again with 700 to 1500 picoamps and stimulated with current of 0.25 mA, pulse duration of 40 pulses/s, pulse width of 100 μs, and frequency of 100 Hz,
3.5 mV, 30 Hz, square wave,
0.25 mA, 3.0V, 100 Hz, 100 μs pulse width, square wave, and
a sequential combination of any thereof.

8. The method according to claim 5, wherein the sixth exogenous bioelectric signal (VEGF) comprises an exogenous bioelectric signal selected from the group consisting of
(a) 100 mV, 10 Hz, pulse width 200 μs, square wave,
(b) 3 V/cm, 10 Hz, 2 microAmps and a pulse duration of 0.2 ms,
(c) 20 V/cm 100 Hz, 0.25 mA (2.5e-7 amps) and pulse duration of 40 pulses/s, width of 100 μs,
(d) first 20V, then 20 mV, current of 0.25 mA, pulse duration of 40 pulses/s, pulse width of 100 μs, and frequency of 100 Hz followed by 528 Hz and 432 Hz and 50 Hz,
(e) 30 pulses per second with a voltage of 3.5 mV, and successively alternating currents of 700 to 1500 picoamps, and again with 700 to 1500 picoamps and stimulated with current of 0.25 mA, pulse duration of 40 pulses/s, pulse width of 100 μs, and frequency of 100 Hz,
(f) 20V/cm, 100 Hz, pulse width 100 μs, square wave,
(g) 3.5 mV, 30 Hz, square wave,
(h) 0.25 mA, 3.0V, 100 Hz, 100 μs pulse width, square wave,
(i) 10V/cm, 500 Hz, pulse width 180 μs, square wave,
(j) 5V, 500 Hz, pulse width 180 μs, square wave,
(k) 3.5V, 10 second burst every 30 seconds, square wave,
(l) alternating high-frequency (HF) and medium-frequency signals (MF) of symmetric, biphasic, trapezoid pulses, with 400-μs pulse duration and 1.5/1-s ramp-up/ramp-down duration, respectively; HF consisting of 75 Hz pulses with 6 seconds on and 21 seconds off; MF consisting of 45 Hz pulses with 5 seconds on and 12 seconds off; and followed by stimulation for both 1 Hz and 20 Hz stimulations, wherein for 1 Hz stimulation, stimulation is applied for 9 seconds, followed by a 1 second silent period, and for 20 Hz stimulation, stimulation is applied for 2 seconds, followed by silent period for 28 seconds,
(m) 100 mV, 50 Hz, square wave, and
(n) a sequential combination of any thereof.

9. The method according to claim 5, further comprising: delivering to the area of skin a skin regeneration composition mix comprising adipose tissue-derived stem cells, exosomes, micro RNAs, hydrogel skin matrix, elastin, oxygenated nanoparticles, platelet rich fibrin ("PRF"), amniotic fluid, and selected growth factors.

10. The method according to claim 5, further comprising: delivering to the area of skin platelet rich fibrin ("PRF").

11. The method according to claim 5, further comprising: delivering to the area of skin amniotic fluid.

12. The method according to claim 5, further comprising: delivering to the area of skin adipose tissue-derived stem cells.

13. The method according to claim 5, further comprising: electrical stimulation with the area of skin conductive electro-massaging gloves.

14. The method according to claim 5, further comprising: conducting electroacupuncture on the area of skin.

15. The method according to claim 5, further comprising: delivering to the area of skin LED pulsed light therapy.

16. The method according to claim 5, further comprising: applying to the area of skin amniotic fluid membrane dressings.

17. The method according to claim 5, further comprising: delivering to the area of skin oxygenated nanoparticles.

18. The method according to claim 5, further comprising: delivering to the area of skin hydrogel skin matrix.

19. The method according to claim 5, further comprising: applying to the area of skin a hydrogel and stem cell matrix-based skin cream.

20. An electrical stimulator comprising a pair of electrodes and a controller that is pre-programmed to produce each of the following bioelectric signals for application to an area of mammalian skin:
a first exogenous bioelectric signal to recruit stem cells to the area of the mammalian skin for about seven (7) minutes,
a second exogenous bioelectric signal of 3 mV with electric frequency of 22 Hz, square wave for about four (4) minutes,
a third exogenous bioelectric signal of 60 mV, 50 Hz, square wave for about twelve (12) minutes, and
a fourth exogenous bioelectric signal to improve blood circulation in the area for about five (5) minutes.

21. An electrical stimulator comprising a pair of electrodes and a controller that is pre-programmed to produce each of the following bioelectric signals for application to an area of mammalian skin:
a first exogenous bioelectric signal to recruit stem cells to the area of the mammalian skin for about seven (7) minutes,
a second exogenous bioelectric signal to differentiate the stem cells into skin cells for about three (3) minutes,
a third exogenous bioelectric signal of 3 mV with electric frequency of 22 Hz, square wave for about four (4) minutes,
a fourth exogenous bioelectric signal of 10V/cm, 500 Hz, pulse width 180 ps, square wave for about three (3) minutes,
a fifth exogenous bioelectric signal of 60 mV, 50 Hz, square wave for about twelve (12) minutes,
a sixth exogenous bioelectric signal to improve blood circulation in the area for about five (5) minutes,
a seventh exogenous bioelectric signal of IOV/cm, 50 Hz, square wave for about two (2) minutes,
an eighth exogenous bioelectric signal selected from the group consisting of (a) 30 pulses per second with a voltage of 3.5 mV, and successively alternating currents of 700 to 1500 pi coamps, and again with 700 to 1500 picoamps and stimulated with current of 0.25 mA, pulse duration of 40 pulses/s, pulse width of 100 ps, and frequency of 100 Hz, (b) 3.5 mV, 30 Hz, square wave, (c) 0.25 mA, 3.0V, 100 Hz, 100 ps pulse width, square wave, (d) a sequential combination of any thereof for about one (1) minute, and
a ninth exogenous bioelectric signal to differentiate the stem cells in the area into skin cells for about one (1) minute.

* * * * *

UNITED STATES PATENT AND TRADEMARK OFFICE
CERTIFICATE OF CORRECTION

PATENT NO. : 11,052,247 B2  
APPLICATION NO. : 16/129533  
DATED : July 6, 2021  
INVENTOR(S) : Leonhardt et al.

Page 1 of 1

It is certified that error appears in the above-identified patent and that said Letters Patent is hereby corrected as shown below:

In the Specification

Column 2, Line 48, change "HIF-1-a" to --HIF-1-α--  
Column 3, Line 4, change "HIF-1-a" to --HIF-1-α--  
Column 3, Line 8, change "re-Tillable" to --re-fillable--  
Column 4, Line 27, change "HIF-1-a" to --HIF-1-α--  
Column 4, Line 39, change "HIF-1-a" to --HIF-1-α--  
Column 4, Line 51, change "HIF-1-a" to --HIF-1-α--  
Column 10, Line 14, change "HIF-1-a" to --HIF-1-α--  
Column 10, Line 38, change "SDF-1" to --SDF-l--

In the Claims

Claim 5, Column 17, Line 32, change "180 ps" to --180 μs--  
Claim 5, Column 17, Line 38, change "IOV" to --10V--  
Claim 5, Column 17, Line 39, change "wave" to --wave,--  
Claim 8, Column 18, Line 23, delete "(VEGF)"  
Claim 21, Column 20, Line 16, change "180 ps" to --180 μs--  
Claim 21, Column 20, Line 22, change "IOV" to --10V--  
Claim 21, Column 20, Line 27, change "pi coamps" to --picoamps--  
Claim 21, Column 20, Line 29, change "100 ps" to --100 μs--  
Claim 21, Column 20, Line 31, change "100 ps" to --100 μs--

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*